(12) United States Patent
Hu et al.

(10) Patent No.: US 6,570,003 B1
(45) Date of Patent: May 27, 2003

(54) HUMAN 7TM PROTEINS AND POLYNUCLEOTIDES ENCODING THE SAME

(75) Inventors: Yi Hu, Spring, TX (US); Michael B. Burnett, Houston, TX (US); Brian Zambrowicz, The Woodlands, TX (US)

(73) Assignee: Lexion Genetics Incorporated, The Woodlands, TX (US)

(*) Notice: Subject to any disclaimer, the term of this patent is extended or adjusted under 35 U.S.C. 154(b) by 2 days.

(21) Appl. No.: 10/042,810

(22) Filed: Jan. 9, 2002

Related U.S. Application Data

(60) Provisional application No. 60/261,624, filed on Jan. 9, 2001.

(51) Int. Cl.[7] ............................................. C07H 21/02
(52) U.S. Cl. ..................................... 536/23.1; 536/23.5
(58) Field of Search ............................. 536/23.1, 23.5

(56) References Cited

U.S. PATENT DOCUMENTS 5,891,720 A * 4/1999 Moore et al.

* cited by examiner

*Primary Examiner*—Jennifer E. Graser

(57) ABSTRACT

The nucleotide and amino acid sequences of two novel human G protein coupled receptors are described.

6 Claims, No Drawings

US 6,570,003 B1

HUMAN 7TM PROTEINS AND POLYNUCLEOTIDES ENCODING THE SAME

The present application claims the benefit of U.S. Provisional Application No. 60/261,624 which was filed on Jan. 9, 2001 and is herein incorporated by reference in its entirety.

1. INTRODUCTION

The present invention relates to the discovery, identification and characterization of novel human polynucleotides that encode membrane associated proteins and receptors. The invention encompasses the described polynucleotides, host cell expression systems, the encoded proteins, fusion proteins, polypeptides and peptides, antibodies to the encoded proteins and peptides, and genetically engineered animals that either lack or overexpress the disclosed genes, antagonists and agonists of the proteins, and other compounds that modulate the expression or activity of the proteins encoded by the disclosed genes, which can be used for diagnosis, drug screening, clinical trial monitoring, the treatment of diseases and disorders, and cosmetic or nutriceutical applications.

2. BACKGROUND OF THE INVENTION

Membrane receptor proteins can serve as integral components of cellular mechanisms for sensing their environment, and maintaining cellular homeostasis and function. Accordingly, membrane receptor proteins are often involved in transduction pathways that control cell physiology, chemical communication, and gene expression. A particularly relevant class of membrane receptors are those typically characterized by the presence of 7 conserved transmembrane domains that are interconnected by nonconserved hydrophilic loops. Such, "7TM receptors" include a superfamily of receptors known as G-protein coupled receptors (GPCRs). GPCRs are typically involved in transduction pathways involving G-proteins or PPG proteins. As such, the GPCR family includes many receptors that are known to serve as drug targets for therapeutic agents.

3. SUMMARY OF THE INVENTION

The present invention relates to the discovery, identification, and characterization of nucleotides that encode novel GPCRs and the corresponding novel GPCR (NGPCR) amino acid sequences. The NGPCRs described for the first time herein are transmembrane proteins that span the cellular membrane and are involved in signal transduction after ligand binding. The described NGPCRs have structural motifs found in the 7TM receptor family. Though the described NGPCRs show strong similarity to a variety of olfactory receptors, expression of the described NGPCRs can also be detected in a variety of human cells and tissues not normally associated with olfactory functions. The novel human GPCR sequences described herein encode proteins of 1248 and 1278 amino acids in length (see respectively SEQ ID NOS: 2 and 4). The described NGPCRs have multiple transmembrane regions (of about 20–30 amino acids) characteristic of 7TM proteins as well as several predicted cytoplasmic domains.

Additionally contemplated are "knockout" ES cells that have been engineered using conventional methods (see, for example, PCT Applic. No. PCT/US98/03243, filed Feb. 20, 1998, herein incorporated by reference). Accordingly, an additional aspect of the present invention includes knockout cells and animals having genetically engineered mutations in the gene encoding the presently described NGPCRs.

The invention encompasses vectors that have been engineered to the nucleotides presented in the Sequence Listing, host cells expressing such vectors, the expression products of such nucleotides, and: (a) nucleotides that encode mammalian homologs of the described NGPCRs, including the specifically described human NGPCRs, as well as the human NGPCR gene products; (b) nucleotides that encode one or more portions of the NGPCRs that correspond to functional domains, and the polypeptide products specified by such nucleotide sequences, including but not limited to the novel regions of the described extracellular domain(s) (ECD), one or more transmembrane domain(s) (TM) first disclosed herein, and the cytoplasmic domain(s) (CD); (c) isolated nucleotides that encode mutants, engineered or naturally occurring, of the described NGPCRs in which all or a part of at least one of the domains is deleted or altered, and the polypeptide products specified by such nucleotide sequences, including but not limited to soluble receptors in which all or a portion of a TM is deleted (in the case of the described 7TM a soluble product can be generated by engineering the protein to upstream from the first TM such that all downstream TMs are deleted), and nonfunctional receptors in which all or a portion of the CD is deleted; (d) nucleotides that encode fusion proteins containing the coding region from an NGPCR, or one of its domains (e.g., an extracellular domain) fused to another peptide or polypeptide.

The invention also encompasses agonists and antagonists of the described NGPCRs, including small molecules, large molecules, mutant NGPCRs, or portions thereof, that compete with native NGPCR, peptides, and antibodies, as well as nucleotide sequences that can be used to inhibit the expression of the described NGPCRs (e.g., antisense and ribozyme molecules, and open reading frame or regulatory sequence replacement constructs) or to enhance the expression of the described NGPCRs (e.g., expression constructs that place the described polynucleotide under the control of a strong promoter system), and transgenic animals that express a NGPCR sequence, or "knock-outs" (which can be conditional) that do not express a functional NGPCR. Knock-out mice can be produced in several ways, one of which involves the use of mouse embryonic stem cells ("ES cells") lines that contain gene trap mutations in a murine homolog of at least one of the described NGPCRs. When the unique NGPCR sequences described in SEQ ID NOS:1–5 are "knocked-out" they provide a method of identifying phenotypic expression of the particular gene as well as a method of assigning function to previously unknown genes. In addition, animals in which the unique NGPCR sequences described in SEQ ID NOS:1–5 are "knocked-out" provide a unique source in which to elicit antibodies to homologous and orthologous proteins which would have been previously viewed by the immune system as "self" and therefore would have failed to elicit significant antibody responses.

Additionally, the unique NGPCR sequences described in SEQ ID NOS:1–5 are useful for the identification of protein coding sequence and mapping a unique gene to a particular chromosome. These sequences identify actual, biologically verified, and therefore relevant, exon splice junctions as opposed to those that may have been bioinformatically predicted from genomic sequence alone. The sequences of the present invention are also useful as additional DNA markers for restriction fragment length polymorphism (RFLP) analysis, and in forensic biology.

Further, the present invention also relates to processes for identifying compounds that modulate, i.e., act as agonists or antagonists, of NGPCR expression and/or NGPCR activity that utilize purified preparations of the described NGPCRs and/or NGPCR product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the described NGPCR ORFs and the amino acid sequences encoded thereby. SEQ ID NO: 5 describes a NGPCR ORF and flanking regions.

5. DETAILED DESCRIPTION OF THE INVENTION

The human NGPCRs described for the first time herein are novel receptor proteins that can be expressed in human fetal brain, pituitary, spinal cord, thymus, spleen, lymph node, liver, prostate, testis, thyroid, adrenal gland, skeletal muscle, uterus, placenta, mammary gland, bladder, rectum, pericardium, ovary, fetal kidney, fetal lung, gall bladder, tongue, aorta, 6-, 9-, and 12-week embryos, adenocarcinoma, osteosarcoma, and endothelial cells. The described NGPCR sequences were obtained using human genomic sequences (GENBANK Accession No. AC068148) in conjunction with cDNAs generated from mRNAs from human fetal brain, lung, and testis cells (Edge Biosystems, Gaithersburg, Md.).

The human NGPCRs described for the first time herein are novel receptor proteins that typically display sequence homology to mammalian olfactory receptors. However, applicants have discovered that the present NGPCRs can be expressed in a variety of human cells beyond olfactory receptors which indicate that the described NGPCRs can play important biology roles in the body. The described NGPCRs are transmembrane proteins of the 7TM family of receptors. As with other GPCRs, signal transduction is triggered when a ligand binds to the receptor. Interfering with the binding of the natural ligand, or neutralizing or removing the ligand, or interference with its binding to a NGPCR will effect NGPCR-mediated signal transduction. Because of their biological significance, 7TM, and particularly GPCR, proteins have been subjected to intense scientific and commercial scrutiny (see, for example, U.S. application Ser. No. 08/820,521, filed Mar. 19, 1997, and Ser. No. 08/833,226, filed Apr. 17, 1997 both of which are herein incorporated by reference in their entirety for applications, uses, and assays involving the described NGPCRs). In addition to 7TM proteins, the presently described NGPCRs share significant homology with GPCRs of the hepta-helical receptor families.

The invention encompasses the use of the described NGPCR nucleotides, NGPCR proteins and peptides, as well as antibodies, preferably humanized monoclonal antibodies, or binding fragments, domains, or fusion proteins thereof, to the NGPCRs (which can, for example, act as NGPCR agonists or antagonists), antagonists that inhibit receptor activity or expression, or agonists that activate receptor activity or increase its expression in the diagnosis and treatment of disease.

In particular, the invention described in the subsections below encompasses NGPCR polypeptides or peptides corresponding to functional domains of NGPCR (e.g., ECD, TM or CD), mutated, truncated or deleted NGPCRs (e.g., NGPCRs missing one or more functional domains or portions thereof, such as, $\Delta$ECD, $\Delta$TM and/or $\Delta$CD), NGPCR fusion proteins (e.g., a NGPCR or a functional domain of a NGPCR, such as the ECD, fused to an unrelated protein or peptide such as an immunoglobulin constant region, i.e., IgFc), nucleotide sequences encoding such products, and host cell expression systems that can produce such NGPCR products.

The invention also encompasses antibodies and anti-idiotypic antibodies (including Fab fragments), antagonists and agonists of the NGPCR, as well as compounds or nucleotide constructs that inhibit expression of a NGPCR gene (transcription factor inhibitors, antisense and ribozyme molecules, or gene or regulatory sequence replacement constructs), or promote expression of NGPCR (e.g., expression constructs in which NGPCR coding sequences are operatively associated with expression control elements such as promoters, promoter/enhancers, etc.). The invention also relates to host cells and animals genetically engineered to express the human NGPCRs (or mutants thereof) or to inhibit or "knock-out" expression of the animal's endogenous NGPCR genes.

The NGPCR proteins or peptides, NGPCR fusion proteins, NGPCR nucleotide sequences, antibodies, antagonists and agonists can be useful for the detection of mutant NGPCRs or inappropriately expressed NGPCRs for the diagnosis of disease. The NGPCR proteins or peptides, NGPCR fusion proteins, NGPCR nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NGPCR in the body. The use of engineered host cells and/or animals may offer an advantage in that such systems allow not only for the identification of compounds that bind to an ECD of a NGPCR, but can also identify compounds that affect the signal transduced by an activated NGPCR.

Finally, the NGPCR protein products (especially soluble derivatives such as peptides corresponding to a NGPCR ECD, or truncated polypeptides lacking on or more TM domains) and fusion protein products (especially NGPCR-Ig fusion proteins, i.e., fusions of a NGPCR, or a domain of a NGPCR, e.g., ECD, $\Delta$TM to an IgFc), antibodies and anti-idiotypic antibodies (including Fab fragments), antagonists or agonists (including compounds that modulate signal transduction which may act on downstream targets in a NGPCR-mediated signal transduction pathway) can be used for therapy of such diseases. For example, the administration of an effective amount of soluble NGPCR ECD, $\Delta$TM, or an ECD-IgFc fusion protein or an anti-idiotypic antibody (or its Fab) that mimics the NGPCR ECD would "mop up" or "neutralize" the endogenous NGPCR ligand, and prevent or reduce binding and receptor activation. Nucleotide constructs encoding such NGPCR products can be used to genetically engineer host cells to express such products in vivo; these genetically engineered cells function as "bioreactors" in the body delivering a continuous supply of a NGPCR, a NGPCR peptide, soluble ECD or $\Delta$TM or a NGPCR fusion protein that will "mop up" or neutralize a NGPCR ligand. Nucleotide constructs encoding functional NGPCRs, mutant NGPCRs, as well as antisense and ribozyme molecules can be used in "gene therapy" approaches for the modulation of NGPCR expression. Thus, the invention also encompasses pharmaceutical formulations and methods for treating biological disorders.

Various aspects of the invention are described in greater detail in the subsections below.

5.1 The NGPCR Polynucleotides

The cDNA sequences and deduced amino acid sequences of the described human NGPCRs are presented in the Sequence Listing. The gene encoding the described NGPCRs is dispersed among a number of exons that are apparently present on human chromosome 8 and/or 18.

The invention also includes oligonucleotides that hybridize to, and are therefore the complements of, the described NGPCR nucleotide sequences. Such oligonucleotides are about 16 to about 100 base long, about 20 to about 80, or about 34 to about 45 base long, or any variation or combination of sizes represented therein incorporating a contiguous region of sequence first disclosed in the present Sequence Listing, can be used in conjunction with the polymerase chain reaction (PCR) to screen libraries, isolate clones, and prepare cloning and sequencing templates, etc.

Alternatively, such NGPCR oligonucleotides can be used as hybridization probes for screening libraries, and assessing gene expression patterns (particularly using a micro array or high-throughput "chip" format). Additionally, a series of the described NGPCR oligonucleotide sequences, or the complements thereof, can be used to represent all or a portion of the described NGPCR sequences. An oligonucleotide or polynucleotide sequence first disclosed in at least a portion of one or more of the sequences of SEQ ID NOS: 1–5 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–5, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–5 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–5.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–5 provides detailed information about transcriptional changes involved in a specific pathway, potentially leading to the identification of novel components or gene functions that manifest themselves as novel phenotypes.

Probes consisting of sequences first disclosed in SEQ ID NOS:1–5 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–5 can be utilized in microarrays or other assay formats, to screen collections of genetic material from patients who have a particular medical condition. These investigations can also be carried out using the sequences first disclosed in SEQ ID NOS:1–5 in silico and by comparing previously collected genetic databases and the disclosed sequences using computer software known to those in the art.

Thus the sequences first disclosed in SEQ ID NOS:1–5 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–5. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NGPCR gene antisense molecules, useful, for example, in NGPCR gene regulation and/or as antisense primers in amplification reactions of NGPCR gene nucleic acid sequences.

The described oligonucleotides may encode or act as NGPCR antisense molecules, useful, for example, in NGPCR gene regulation (for and/or as antisense primers in amplification reactions of NGPCR gene nucleic acid sequences). With respect to NGPCR gene regulation, such techniques can be used to regulate biological functions. Further, such sequences may be used as part of ribozyme and/or triple helix sequences, also useful for NGPCR gene regulation.

Additionally, the antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. USA 85:7448–7451), etc.

Low stringency conditions are well-known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Spring Harbor Press, NY; and Ausubel et al., 1989, Current Protocols in Molecular Biology, Green Publishing Associates and Wiley Interscience, NY.

NGPCR homologs can be isolated from the nucleic acid of the organism of interest by performing PCR using two degenerate oligonucleotide primer pools designed on the basis of amino acid sequences within the NGPCR gene product disclosed herein. The template for the reaction may be total RNA, mRNA, and/or cDNA obtained by reverse transcription of mRNA prepared from, for example, human or non-human cell lines or tissue known or suspected to express a NGPCR gene allele.

The PCR product may be subcloned and sequenced to ensure that the amplified sequences represent the sequence of the desired NGPCR gene. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences corresponding to the described NGPCRs. For example, RNA may be isolated, following standard procedures, from an appropriate cellular or tissue source (i.e., one known, or suspected, to express a NGPCR gene). A reverse transcription (RT) reaction may be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment may easily be isolated. For a review of cloning strategies which may be used, see e.g., Sambrook et al., 1989, supra.

A cDNA of a mutant NGPCR sequence can also be isolated, for example, by using PCR. In this case, the first cDNA strand may be synthesized by hybridizing an oligo-dT oligonucleotide to mRNA isolated from tissue known or suspected to be expressed in an individual putatively carrying a mutant NGPCR allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well-known to those of skill in the art. By comparing the DNA sequence of the mutant NGPCR allele to that of the normal NGPCR allele, the mutation(s) responsible for the loss or alteration of function of the mutant NGPCR gene product can be ascertained.

Alternatively, a genomic library can be constructed using DNA obtained from an individual suspected of or known to carry the mutant NGPCR allele, or a cDNA library can be constructed using RNA from a tissue known, or suspected, to express the mutant NGPCR allele. A normal NGPCR gene, or any suitable fragment thereof, can then be labeled and used as a probe to identify the corresponding mutant NGPCR allele in such libraries. Clones containing the mutant NGPCR sequences can then be purified and subjected to sequence analysis according to methods well-known to those of skill in the art.

Additionally, an expression library can be constructed utilizing cDNA synthesized from, for example, RNA isolated from a tissue known, or suspected, to express a mutant NGPCR allele in an individual suspected of or known to carry such a mutant allele. In this manner, gene products made by the putatively mutant tissue may be expressed and screened using standard antibody screening techniques in conjunction with antibodies raised against the normal NGPCR gene product, as described below. For screening techniques, see, for example, Harlow, E. and Lane, eds., 1988, "Antibodies: A Laboratory Manual", Cold Spring Harbor Press, Cold Spring Harbor, N.Y.

Additionally, screening can be accomplished by screening with labeled NGPCR fusion proteins, such as, for example, alkaline phosphatase-NGPCR or NGPCR-alkaline phosphatase fusion proteins. In cases where a NGPCR mutation results in an expressed product with altered function (e.g., as a result of a missense or a frameshift mutation), a polyclonal set of antibodies to NGPCR are likely to cross-react with the mutant NGPCR gene product. Library clones detected via their reaction with such labeled antibodies can be purified and subjected to sequence analysis according to methods well-known to those of skill in the art.

The invention also encompasses nucleotide sequences that encode mutant NGPCRs, peptide fragments of the NGPCRs, truncated NGPCRs, and NGPCR fusion proteins. These include, but are not limited to, nucleotide sequences encoding mutant NGPCRs described below; polypeptides or peptides corresponding to one or more ECD, TM and/or CD domains of the NGPCR or portions of these domains; truncated NGPCRs in which one or two of the domains is deleted, e.g., a soluble NGPCR lacking the TM or both the TM and CD regions, or a truncated, nonfunctional NGPCR lacking all or a portion of the CD region. Nucleotides encoding fusion proteins may include, but are not limited to, full length NGPCR sequences, truncated NGPCRs, or nucleotides encoding peptide fragments of NGPCR fused to an unrelated protein or peptide, such as for example, a transmembrane sequence, which anchors the NGPCR ECD to the cell; an IgFc domain which increases the stability and half life of the resulting fusion protein (e.g., NGPCR-Ig) in the bloodstream; or an enzyme, fluorescent protein, luminescent protein which can be used as a marker.

The invention also encompasses (a) DNA vectors that contain any of the foregoing NGPCR coding sequences and/or their complements (i.e., antisense); (b) DNA expression vectors that contain any of the foregoing NGPCR coding sequences operatively associated with a regulatory element that directs the expression of the coding sequences; and (c) genetically engineered host cells that express an endogenous NGPCR sequence under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of a NGPCR, as well as compounds or nucleotide constructs that inhibit expression of a NGPCR sequence (transcription factor inhibitors, antisense and ribozyme molecules, or open reading frame sequence or regulatory sequence replacement constructs), or promote the expression of a NGPCR (e.g., expression constructs in which NGPCR coding sequences are operatively associated with expression control elements such as promoters, promoter/enhancers, etc.).

5.2 NGPCR Proteins and Polypeptides

NGPCR proteins, polypeptides and peptide fragments, mutated, truncated or deleted forms of the NGPCR and/or NGPCR fusion proteins can be prepared for a variety of uses. These uses include, but are not limited to, the generation of antibodies, as reagents in diagnostic assays, the identification of other cellular gene products related to a NGPCR, as reagents in assays for screening for compounds that can be used as pharmaceutical reagents useful in the therapeutic treatment of mental, biological, or medical disorders (i.e., kidney disorders, improper blood pressure, etc.) and disease. The described NGPCRs share structural similarity with, but not limited to, SLIT proteins, LIG-1 protein, and insulin-like growth factor binding proteins.

The Sequence Listing discloses the amino acid sequences encoded by the described NGPCR genes. The NGPCRs have initiator methionines in DNA sequence contexts consistent with translation initiation sites but do not display N-terminal hydrophobic signal sequences typical of other membrane associated proteins or secreted proteins. The sequence data presented herein indicate that alternatively spliced forms of the NGPCRs exist.

Transcripts encoding these NGPCRs can be found (using RT-PCR) expressed in expressed in human fetal brain, pituitary, spinal cord, thymus, spleen, lymph node, liver, prostate, testis, thyroid, adrenal gland, skeletal muscle, uterus, placenta, mammary gland, bladder, rectum, pericardium, ovary, fetal kidney, fetal lung, gall bladder, tongue, aorta, 6-, 9-, and 12-week embryos, adenocarcinoma, osteosarcoma, and endothelial cells. The described NGPCR sequences were obtained using human genomic sequences (GENBANK Accession No. AC068148) in conjunction with cDNAs generated from mRNAs from human fetal brain, lung, and testis cells (Edge Biosystems, Gaithersburg, Md.).

The NGPCR amino acid sequences of the invention include the amino acid sequences presented in the Sequence Listing as well as analogues and derivatives thereof. Further, corresponding NGPCR homologues from other species are encompassed by the invention. In fact, any NGPCR protein encoded by the NGPCR nucleotide sequences described above are within the scope of the invention, as are any novel polynucleotide sequences encoding all or any novel portion of an amino acid sequence presented in the Sequence Listing. The degenerate nature of the genetic code is well-known, and, accordingly, each amino acid presented in the Sequence Listing, is generically representative of the well-known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NGPCR encoded by the described nucleotide sequences as judged by any of a number of criteria, including but not limited to the ability to bind a ligand for a NGPCR, the ability to effect an identical or complementary signal transduction pathway, a change in cellular metabolism (e.g., ion flux, tyrosine phosphorylation, etc.) or change in phenotype when the NGPCR equivalent is present in an appropriate cell-type (such as the amelioration, prevention or delay of a biochemical, biophysical, or overt phenotype. Such functionally equivalent NGPCR proteins include but are not limited to additions or substitutions of amino acid residues within the amino acid sequence encoded by the NGPCR nucleotide sequences described above but which result in a silent change, thus producing a functionally equivalent expression product. Amino acid substitutions may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

While random mutations can be made to NGPCR DNA (using. random mutagenesis techniques well-known to those skilled in the art) and the resulting mutant NGPCRs tested for activity, site-directed mutations of the NGPCR coding sequence can be engineered (using site-directed mutagenesis techniques well-known to those skilled in the art) to generate mutant NGPCRs with increased function, e.g., higher binding affinity for the target ligand, and/or greater signaling capacity; or decreased function, and/or decreased signal transduction capacity. One starting point for such analysis is by aligning the disclosed human sequences with corresponding gene/protein sequences from, for example, other mammals in order to identify amino acid sequence motifs that are conserved between different species. Non-conservative changes can be engineered at variable positions to alter function, signal transduction capability, or both. Alternatively, where alteration of function is desired, deletion or non-conservative alterations of the conserved regions (i.e., identical amino acids) can be engineered. For example, deletion or non-conservative alterations (substitutions or insertions) of the various conserved transmembrane domains.

An additional application of the described NGPCR polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721, 5,723,323, and 5,837,458 which are herein incorporated by reference in their entirety.

Additionally contemplated uses for the described sequences include the engineering of constitutively "on" variants for use in cell assays and genetically engineered animals using the methods and applications described in U.S. patent applications Ser. Nos. 60/110,906, 60/106,300, 60/094,879, and 60/121,851 all of which are herein incorporated by reference in their entirety.

Other mutations in the NGPCR coding sequence can be made to generate NGPCRs that are better suited for expression, scale up, etc. in the host cells chosen. For example, cysteine residues can be deleted or substituted with another amino acid in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur in the ECD (N-X-S or N-X-T), and/or an amino acid deletion at the second position of any one or more such recognition sequences in the ECD will prevent glycosylation of the NGPCR at the modified tripeptide sequence. (See, e.g., Miyajima et al., 1986, EMBO J. 5(6):1193–1197).

Peptides corresponding to one or more domains of the NGPCR (e.g., ECD, TM, CD, etc.), truncated or deleted NGPCRs (e.g., NGPCR in which a ECD, TM and/or CD is deleted) as well as fusion proteins in which a full length NGPCR, a NGPCR peptide, or truncated NGPCR is fused to an unrelated protein, are also within the scope of the invention and can be designed on the basis of the presently disclosed NGPCR nucleotide and NGPCR amino acid sequences. Such fusion proteins include but are not limited to IgFc fusions which stabilize the NGPCR protein or peptide and prolong half-life in vivo; or fusions to any amino acid sequence that allows the fusion protein to be anchored to the cell membrane, allowing an ECD to be exhibited on the cell surface; or fusions to an enzyme, fluorescent protein, or luminescent protein which provide a marker function.

While the NGPCR polypeptides and peptides can be chemically synthesized (e.g., see Creighton, 1983, Proteins: Structures and Molecular Principles, W.H. Freeman & Co., NY.), large polypeptides derived from a NGPCR and full length NGPCRs can be advantageously produced by recombinant DNA technology using techniques well-known in the art for expressing nucleic acid containing NGPCR gene sequences and/or coding sequences. Such methods can be used to construct expression vectors containing a presently described NGPCR nucleotide sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA corresponding to all or a portion of a transcript encoded by a NGPCR nucleotide sequence may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the NGPCR nucleotide sequences of the invention. Where the NGPCR peptide or polypeptide is a soluble derivative (e.g., NGPCR peptides corresponding to an ECD; truncated or deleted NGPCR in which a TM and/or CD are deleted) the peptide or polypeptide can be recovered from the culture, i.e., from the host cell in cases where the NGPCR peptide or polypeptide is not secreted, and from the culture media in cases where the NGPCR peptide or polypeptide is secreted by the cells. However, such expression systems also encompass engineered host cells that express a NGPCR, or functional equivalent, in situ, i.e., anchored in the cell membrane. Purification or enrichment of NGPCR from such expression systems can be accomplished using appropriate detergents and lipid micelles and methods well-known to those skilled in the art. However, such engineered host cells themselves may be used in situations where it is important not only to retain the structural and functional characteristics of the NGPCR, but to assess biological activity, e.g., in certain drug screening assays.

The expression systems that may be used for purposes of the invention include, but are not limited to, microorganisms such as bacteria (e.g., *E. coli, B. subtilis*) transformed with recombinant bacteriophage DNA, plasmid DNA or cosmid DNA expression vectors containing NGPCR nucleotide sequences; yeast (e.g., Saccharomyces, Pichia) transformed with recombinant yeast expression vectors containing NGPCR nucleotide sequences; insect cell systems infected with recombinant virus expression vectors (e.g., baculovirus) containing NGPCR nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NGPCR nucleotide sequences; or mammalian cell systems (e.g., COS, CHO, BHK, 293, 3T3) harboring recombinant expression constructs containing NGPCR nucleotide sequences and promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NGPCR gene product being expressed. For example, when a large quantity of such a protein is to be produced, for the generation of pharmaceutical compositions of NGPCR protein or for raising antibodies to a NGPCR protein, for example, vectors that direct the expression of high levels of fusion protein products that are readily purified may be desirable. Such vectors include, but are not limited to, the *E. coli* expression vector pUR278 (Ruther et al., 1983, EMBO J. 2:1791), in which a NGPCR coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target expression product can be released from the GST moiety.

In an insect system, *Autographa californica* nuclear polyhedrosis virus (AcNPV) is used as a vector to express foreign polynucleotide sequences. The virus grows in *Spodoptera frugiperda* cells. A NGPCR coding sequence can be cloned individually into non-essential regions (for example the polyhedrin gene) of the virus and placed under control of an AcNPV promoter (for example the polyhedrin promoter). Successful insertion of NGPCR coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NGPCR nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NGPCR gene product in infected hosts (e.g., See Logan & Shenk, 1984, Proc. Natl. Acad. Sci. USA 81:3655–3659). Specific initiation signals may also be required for efficient translation of inserted NGPCR nucleotide sequences. These signals include the ATG initiation codon and adjacent sequences. In cases where an entire NGPCR gene or cDNA, including its own initiation codon and adjacent sequences, is inserted into the appropriate expression vector, no additional translational control signals may be needed. However, in cases where only a portion of a NGPCR coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NGPCR sequences described above may be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express a NGPCR gene product. Such engineered cell lines may be particularly useful in screening and evaluation of compounds that affect the endogenous activity of the NGPCR gene product.

A number of selection systems may be used, including but not limited to the herpes simplex virus thymidine kinase (Wigler et al., 1977, Cell 11:223), hypoxanthine-guanine phosphoribosyltransferase (Szybalska and Szybalski, 1962, Proc. Natl. Acad. Sci. USA 48:2026), and adenine phosphoribosyltransferase (Lowy et al., 1980, Cell 22:817) genes, which can be employed in tk⁻, hgprt⁻ or aprt⁻ cells, respectively. Also, antimetabolite resistance can be used as the basis of selection for the following genes: dhfr, which confers resistance to methotrexate (Wigler et al., 1980, Proc. Natl. Acad. Sci. USA 77:3567; O'Hare et al., 1981, Proc. Natl. Acad. Sci. USA 78:1527); gpt, which confers resistance to mycophenolic acid (Mulligan and Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$·nitriloacetic acid-agarose columns and histidine-tagged proteins are selectively eluted with imidazole-containing buffers.

Also encompassed by the present invention are fusion proteins that direct the NGPCR to a target organ and/or facilitate transport across the membrane into the cytosol. Conjugation of NGPCRs to antibody molecules or their Fab fragments could be used to target cells bearing a particular epitope. Attaching the appropriate signal sequence to the NGPCR would also transport the NGPCR to the desired location within the cell. Alternatively targeting of NGPCR or its nucleic acid sequence might be achieved using liposome or lipid complex based delivery systems. Such technologies are described in "Liposomes:A Practical Approach", New, R.R.C., ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NGPCR to the target site or desired organ, where they cross the cell membrane and/or the nucleus where the NGPCR can exert its functional activity. This goal may be achieved by coupling of the NGPCR to a cytokine or other ligand that provides targeting specificity, and/or to a protein transducing domain (see generally U.S. applications Ser. Nos. 60/111, 701 and 60/056,713, both of which are herein incorporated by reference, for examples of such transducing sequences) to facilitate passage across cellular membranes and can optionally be engineered to include nuclear localization.

NGPCR gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NGPCR transgenic animals.

Any technique known in the art may be used to introduce a NGPCR transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus-mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NGPCR transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell-type by following, for example, the teaching of Lasko et al., 1992, Proc. Natl. Acad. Sci. USA 89:6232–6236. The regulatory sequences required for such a cell-type specific activation will depend upon the particular cell-type of interest, and will be apparent to those of skill in the art.

When it is desired that a NGPCR transgene be integrated into the chromosomal site of the endogenous NGPCR gene, gene targeting is preferred. Briefly, when such a technique is to be utilized, vectors containing some nucleotide sequences homologous to the endogenous NGPCR gene are designed for the purpose of integrating, via homologous recombination with chromosomal sequences, into and disrupting the function of the nucleotide sequence of the endogenous NGPCR gene (i.e., "knockout" animals).

The transgene can also be selectively introduced into a particular cell-type, thus inactivating the endogenous NGPCR gene in only that cell-type, by following, for example, the teaching of Gu et al., 1994, Science, 265:103–106. The regulatory sequences required for such a cell-type specific inactivation will depend upon the particular cell-type of interest, and will be apparent to those of skill in the art.

Once transgenic animals have been generated, the expression of the recombinant NGPCR gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of NGPCR gene-expressing tissue, may also be evaluated immunocytochemically using antibodies specific for the NGPCR transgene product.

The present invention provides for "knockin" animals. Knockin animals are those in which a gene that the animal does not naturally have in its genome, is inserted. For example, when a human gene is used to replace its murine ortholog in the mouse. Such knockin animals are useful for the in vivo study, testing and validation of, intra alia, human drug targets as well as for compounds that are directed at the same.

5.3 Antibodies to NGPCR Proteins

Antibodies that specifically recognize one or more epitopes of a NGPCR, or epitopes of conserved variants of a NGPCR, or peptide fragments of a NGPCR are also encompassed by the invention. Such antibodies include but are not limited to polyclonal antibodies, monoclonal antibodies (mAbs), humanized or chimeric antibodies, single chain antibodies, Fab fragments, F(ab')₂ fragments, fragments produced by a Fab expression library, anti-idiotypic (anti-Id) antibodies, and epitope-binding fragments of any of the above.

The antibodies of the invention may be used, for example, in the detection of NGPCR in a biological sample and may, therefore, be utilized as part of a diagnostic or prognostic technique whereby patients may be tested for abnormal amounts of NGPCR. Such antibodies may also be utilized in conjunction with, for example, compound screening schemes for the evaluation of the effect of test compounds on expression and/or activity of a NGPCR expression product. Additionally, such antibodies can be used in conjunction gene therapy to, for example, evaluate the normal and/or engineered NGPCR-expressing cells prior to their introduction into the patient. Such antibodies may additionally be used as a method for the inhibition of abnormal NGPCR activity. Thus, such antibodies may, therefore, be utilized as part of weight disorder treatment methods.

For the production of antibodies, various host animals may be immunized by injection with the NGPCR, an NGPCR peptide (e.g., one corresponding to a functional domain of the receptor, such as an ECD, TM or CD), truncated NGPCR polypeptides (NGPCR in which one or more domains, e.g., a TM or CD, has been deleted), functional equivalents of the NGPCR or mutants of the NGPCR. Such host animals may include but are not limited to rabbits, mice, and rats, to name but a few. Various adjuvants may be used to increase the immunological response, depending on the host species, including, but not limited to, Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diphtheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci. USA 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used (see U.S. Pat. Nos. 6,075,181 and 5,877,397 which are herein incorporated by reference in their entirety). A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150,584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NGPCR expression products.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NGPCR gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NGPCR can, in turn, be utilized to generate anti-idiotype antibodies that "mimic" a given NGPCR, using techniques well-known to those skilled in the art. (See, e.g., Greenspan & Bona, 1993, FASEB J 7(5): 437–444; and Nissinoff, 1991, J. Immunol. 147(8): 2429–2438). For example antibodies which bind to a NGPCR ECD and competitively inhibit the binding of a ligand of NGPCR can be used to generate anti-idiotypes that "mimic" a NGPCR ECD and, therefore, bind and neutralize a ligand. Such neutralizing anti-idiotypes or Fab fragments of such anti-idiotypes can be used in therapeutic regimens involving the NGPCR signaling pathway.

Additionally given the high degree of relatedness of mammalian NGPCRs, the presently described knock-out mice (having never seen NGPCR, and thus never been tolerized to NGPCR) have a unique utility, as they can be advantageously applied to the generation of antibodies against the disclosed mammalian NGPCR (i.e., NGPCR will be immunogenic in NGPCR knock-out animals).

5.4 Diagnosis of Abnormalities Related to a NGPCR

A variety of methods can be employed for the diagnostic and prognostic evaluation of disorders related to NGPCR function, and for the identification of subjects having a predisposition to such disorders.

Such methods can, for example, utilize reagents such as the NGPCR nucleotide sequences described in Section 5.1, and NGPCR antibodies, as described, in Section 5.3. Specifically, such reagents may be used, for example, for: (1) the detection of the presence of NGPCR gene mutations, or the detection of either over- or under-expression of NGPCR mRNA relative to a given phenotype; (2) the detection of either an over- or an under-abundance of NGPCR gene product relative to a given phenotype; and (3) the detection of perturbations or abnormalities in the signal transduction pathway mediated by NGPCR.

The methods described herein may be performed, for example, by utilizing pre-packaged diagnostic kits comprising at least one specific NGPCR nucleotide sequence or NGPCR antibody reagent described herein, which may be conveniently used, e.g., in clinical settings, to diagnose patients exhibiting body weight disorder abnormalities.

For the detection of NGPCR mutations, any nucleated cell can be used as a starting source for genomic nucleic acid. For the detection of NGPCR gene expression or NGPCR gene products, any cell-type or tissue in which the NGPCR gene is expressed can be utilized.

Nucleic acid-based detection techniques and peptide detection techniques are described below.

5.4.1 Detection of NGPCR Genes and Transcripts

Mutations within a NGPCR gene can be detected by utilizing a number of techniques. Nucleic acid from any nucleated cell can be used as the starting point for such assay techniques, and may be isolated according to standard nucleic acid preparation procedures which are well-known to those of skill in the art.

DNA may be used in hybridization or amplification assays of biological samples to detect abnormalities involving NGPCR gene structure, including point mutations, insertions, deletions and chromosomal rearrangements. Such assays may include, but are not limited to, Southern analyses, single stranded conformational polymorphism analyses (SSCP), and PCR analyses.

Such diagnostic methods for the detection of NGPCR gene-specific mutations can involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described in Section 5.1, under conditions favorable for the specific annealing of these reagents to their complementary sequences within a given NGPCR gene. Preferably, the lengths of these nucleic acid reagents are at least 15 to 30 nucleotides. After incubation, all non-annealed nucleic acids are removed from the nucleic acid:NGPCR molecule hybrid. The presence of nucleic acids which have hybridized, if any such molecules exist, is then detected. Using such a detection scheme, the nucleic acid from the cell-type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled NGPCR nucleic acid reagents is accomplished using standard techniques well-known to those in the art. The NGPCR gene sequences to which the nucleic acid reagents have annealed can be compared to the annealing pattern expected from a normal NGPCR gene sequence in order to determine whether a NGPCR gene mutation is present.

Alternative diagnostic methods for the detection of NGPCR gene specific nucleic acid molecules, in patient samples or other appropriate cell sources, may involve their amplification, e.g., by PCR (the experimental embodiment set forth in Mullis, K. B., 1987, U.S. Pat. No. 4,683,202), followed by the detection of the amplified molecules using techniques well-known to those of skill in the art. The resulting amplified sequences can be compared to those which would be expected if the nucleic acid being amplified contained only normal copies of a NGPCR gene in order to determine whether a NGPCR gene mutation exists.

Additionally, well-known genotyping techniques can be performed to identify individuals carrying NGPCR gene mutations. Such techniques include, for example, the use of restriction fragment length polymorphisms (RFLPs), which involve sequence variations in one of the recognition sites for the specific restriction enzyme used.

Additionally, improved methods for analyzing DNA polymorphisms which can be utilized for the identification of NGPCR gene mutations have been described which capitalize on the presence of variable numbers of short, tandemly repeated DNA sequences between the restriction enzyme sites. For example, Weber (U.S. Pat. No. 5,075,217, which is incorporated herein by reference in its entirety) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers which are so closely spaced exhibit a high frequency co-inheritance, and are extremely useful in the identification of genetic mutations, such as, for example, mutations within a given NGPCR gene, and the diagnosis of diseases and disorders related to NGPCR mutations.

Also, Caskey et al. (U.S. Pat. No. 5,364,759, which is incorporated herein by reference in its entirety) describe a DNA profiling assay for detecting short tri and tetra nucleotide repeat sequences. The process includes extracting the DNA of interest, such as the NGPCR gene, amplifying the extracted DNA, and labeling the repeat sequences to form a genotypic map of the individual's DNA.

The level of NGPCR gene expression can also be assayed by detecting and measuring NGPCR transcription. For example, RNA from a cell-type or tissue known, or suspected to express the NGPCR gene can be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the NGPCR gene. Such analyses may reveal both quantitative and qualitative aspects of the expression pattern of the NGPCR gene, including activation or inactivation of NGPCR gene expression.

In one embodiment of such a detection scheme, cDNAs are synthesized from the RNAs of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the NGPCR nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining, by utilizing any other suitable nucleic acid staining method, or by sequencing.

Additionally, it is possible to perform such NGPCR gene expression assays "in situ", i.e., directly upon tissue sections (fixed and/or frozen) of patient tissue obtained from biopsies or resections, such that no nucleic acid purification is necessary. Nucleic acid reagents such as those described above may be used as probes and/or primers for such in situ procedures (See, for example, Nuovo, G. J., 1992, "PCR In Situ Hybridization: Protocols And Applications", Raven Press, N.Y.).

Alternatively, if a sufficient quantity of the appropriate cells can be obtained, standard Northern analysis can be performed to determine the level of NGPCR mRNA expression.

5.4.2 Detection of NGPCR Gene Products

Antibodies directed against wild type or mutant NGPCR gene products or conserved variants or peptide fragments thereof, which are discussed above, may also be used as diagnostics and prognostics, as described herein. Such diagnostic methods, may be used to detect abnormalities in the level of NGPCR gene expression, or abnormalities in the structure and/or temporal, tissue, cellular, or subcellular location of the NGPCR, and may be performed in vivo or in vitro, such as, for example, on biopsy tissue.

For example, antibodies directed to epitopes of the NGPCR ECD can be used in vivo to detect the pattern and level of expression of the NGPCR in the body. Such antibodies can be labeled, e.g., with a radio-opaque or other appropriate compound and injected into a subject in order to visualize binding to the NGPCR expressed in the body using methods such as X-rays, CAT-scans, or MRI. Labeled antibody fragments, e.g., the Fab or single chain antibody comprising the smallest portion of the antigen binding region, are preferred for this purpose to promote crossing the blood-brain barrier and permit labeling NGPCRs expressed in the brain.

Additionally, any NGPCR fusion protein or NGPCR conjugated protein whose presence can be detected, can be administered. For example, NGPCR fusion or conjugated proteins labeled with a radio-opaque or other appropriate compound can be administered and visualized in vivo, as discussed, above for labeled antibodies. Further such NGPCR fusion proteins as AP-NGPCR on NGPCR-Ap fusion proteins can be utilized for in vitro diagnostic procedures.

Alternatively, immunoassays or fusion protein detection assays, as described above, can be utilized on biopsy and autopsy samples in vitro to permit assessment of the expression pattern of the NGPCR. Such assays are not confined to the use of antibodies that define a NGPCR ECD, but can include the use of antibodies directed to epitopes of any of the domains of a NGPCR, e.g., the ECD, the TM and/or CD. The use of each or all of these labeled antibodies will yield useful information regarding translation and intracellular transport of the NGPCR to the cell surface, and can identify defects in processing.

The tissue or cell-type to be analyzed will generally include those which are known, or suspected, to express the NGPCR gene. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of a NGPCR gene.

For example, antibodies, or fragments of antibodies, such as those described, above, in Section 5.3, useful in the present invention may be used to quantitatively or qualitatively detect the presence of NGPCR gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred if such NGPCR gene products are expressed on the cell surface.

The antibodies (or fragments thereof) or NGPCR fusion or conjugated proteins useful in the present invention may, additionally, be employed histologically, as in immunofluorescence, immunoelectron microscopy or non-immuno assays, for in situ detection of NGPCR gene products or conserved variants or peptide fragments thereof, or for NGPCR binding (in the case of labeled NGPCR ligand fusion protein).

In situ detection may be accomplished by removing a histological specimen from a patient, and applying thereto a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of a NGPCR gene product, or conserved variants or peptide fragments, or NGPCR binding, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for NGPCR gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying NGPCR gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled NGPCR antibody or NGPCR ligand fusion protein. The solid phase support may then be washed with the buffer a second time to remove unbound antibody or fusion protein. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material can have virtually any possible structural configuration so long as the coupled molecule is capable of binding to an antigen or antibody.

Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of NGPCR antibody or NGPCR ligand fusion protein may be determined according to well-known methods. Those skilled in the art will be able to determine operative and optimal assay conditions for each determination by employing routine experimentation.

With respect to antibodies, one of the ways in which the NGPCR antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme that is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect NGPCR through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.5 Screening Assays for Compounds that Modulate NGPCR Expression or Activity The following assays are designed to identify compounds that interact with (e.g., bind to) NGPCRs (including, but not limited to an ECD or CD of a NGPCR), compounds that interact with (e.g., bind to) intracellular proteins that interact with NGPCR (including but not limited to the TM and CD of NGPCR), compounds that interfere with the interaction of NGPCR with transmembrane or intracellular proteins involved in NGPCR-mediated signal transduction, and to compounds which modulate the activity of NGPCR gene (i.e., modulate the level of NGPCR gene expression) or modulate the level of NGPCR. Assays may additionally be utilized which identify compounds which bind to NGPCR gene regulatory sequences (e.g., promoter sequences) and which may modulate NGPCR gene expression. See e.g., Platt, K. A., 1994, J. Biol. Chem. 269:28558–28562, which is incorporated herein by reference in its entirety.

The compounds that can be screened in accordance with the invention include but are not limited to peptides, antibodies and fragments thereof, and other organic compounds (e.g., peptidomimetics) that bind to an ECD of a NGPCR and either mimic the activity triggered by the natural ligand (i.e., agonists) or inhibit the activity triggered by the natural ligand (i.e., antagonists); as well as peptides, antibodies or fragments thereof, and other organic compounds that mimic the ECD of the NGPCR (or a portion thereof) and bind to and "neutralize" the natural ligand.

Such compounds may include, but are not limited to, peptides such as, for example, soluble peptides, including but not limited to members of random peptide libraries; (see, e.g., Lam, K. S. et al., 1991, Nature 354:82–84; Houghten, R. et al., 1991, Nature 354:84–86), and combinatorial chemistry-derived molecular library made of D- and/or L-configuration amino acids, phosphopeptides (including, but not limited to members of random or partially degenerate, directed phosphopeptide libraries; see, e.g., Songyang, Z. et al., 1993, Cell 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Other compounds which can be screened in accordance with the invention include but are not limited to small organic molecules that are able to cross the blood-brain barrier, gain entry into an appropriate cell (e.g., in the cerebellum, the hypothalamus, etc.) and affect the expression of a NGPCR gene or some other gene involved in the NGPCR signal transduction pathway (e.g., by interacting with the regulatory region or transcription factors involved in gene expression); or such compounds that affect the activity of the NGPCR (e.g., by inhibiting or enhancing the enzymatic activity of a CD) or the activity of some other intracellular factor involved in the NGPCR signal transduction pathway.

Computer modeling and searching technologies permit identification of compounds, or the improvement of already identified compounds, that can modulate NGPCR expression or activity. Having identified such a compound or composition, the active sites or regions are identified. Such active sites might typically be ligand binding sites. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential NGPCR modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of a NGPCR, and related transduction and transcription factors will be apparent to those of skill in the art.

Examples of molecular modeling systems are the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988, Acta Pharmaceutical Fennica 97:159–166; Ripka, New Scientist 54–57 (Jun. 16, 1988); McKinaly and Rossmann, 1989, Annu. Rev. Pharmacol. Toxiciol. 29:111–122; Perry and Davies, OSAR: Quantitative Structure-Activity Relationships in Drug Design pp. 189–193 (Alan R. Liss, Inc. 1989); Lewis and Dean, 1989 Proc. R. Soc. Lond. 236:125–140 and 141–162; and, with respect to a model receptor for nucleic acid components, Askew, et al., 1989, J. Am. Chem. Soc. 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Cell-based systems can also be used to identify compounds that bind NGPCRs as well as assess the altered activity associated with such binding in living cells. One tool of particular interest for such assays is green fluorescent protein which is described, inter alia, in U.S. Pat. No. 5,625,048, herein incorporated by reference. Cells that may be used in such cellular assays include, but are not limited to, leukocytes, or cell lines derived from leukocytes, lymphocytes, stem cells, including embryonic stem cells, and the like. In addition, expression host cells (e.g., B95 cells, COS cells, CHO cells, OMK cells, fibroblasts, Sf9 cells) genetically engineered to express a functional NGPCR of interest and to respond to activation by the test, or natural, ligand, as measured by a chemical or phenotypic change, or induction of another host cell gene, can be used as an end point in the assay.

Compounds identified via assays such as those described herein may be useful, for example, in elaborating the biological function of a NGPCR gene product. Such compounds can be administered to a patient at therapeutically effective doses to treat any of a variety of physiological or mental disorders. A therapeutically effective dose refers to that amount of the compound sufficient to result in any amelioration, impediment, prevention, or alteration of any biological or overt symptom.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral, intracranial, topical, intrathecal, or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

5.5.1 In Vitro Screening Assays for Compounds that Bind to NGPCRs

In vitro systems can be designed to identify compounds capable of interacting with (e.g., binding to) NGPCR (including, but not limited to, a ECD or CD of NGPCR). Compounds identified may be useful, for example, in modulating the activity of wild type and/or mutant NGPCR gene products; may be useful in elaborating the biological function of the NGPCR; may be utilized in screens for identifying compounds that disrupt normal NGPCR interactions; or may in themselves disrupt such interactions.

The principle of the assays used to identify compounds that bind to the NGPCR involves preparing a reaction mixture of the NGPCR and the test compound under conditions and for a time sufficient to allow the two components to interact and bind, thus forming a complex which can be removed and/or detected in the reaction mixture. The NGPCR species used can vary depending upon the goal of the screening assay. For example, where agonists of the natural ligand are sought, the full length NGPCR, or a soluble truncated NGPCR, e.g., in which the TM and/or CD is deleted from the molecule, a peptide corresponding to a ECD or a fusion protein containing one or more NGPCR ECD fused to a protein or polypeptide that affords advantages in the assay system (e.g., labeling, isolation of the resulting complex, etc.) can be utilized. Where compounds that interact with the cytoplasmic domain are sought to be identified, peptides corresponding to the NGPCR CD and fusion proteins containing the NGPCR CD can be used.

The screening assays can be conducted in a variety of ways. For example, one method to conduct such an assay would involve anchoring the NGPCR protein, polypeptide, peptide or fusion protein or the test substance onto a solid phase and detecting NGPCR/test compound complexes anchored on the solid phase at the end of the reaction. In one embodiment of such a method, the NGPCR reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for a NGPCR protein, polypeptide, peptide or fusion protein or the test compound to anchor any complexes formed in solution, and a labeled antibody specific for the other component of the possible complex to detect anchored complexes.

Alternatively, cell-based assays can be used to identify compounds that interact with NGPCR. To this end, cell lines that express NGPCR, or cell lines (e.g., COS cells, CHO cells, fibroblasts, etc.) that have been genetically engineered to express a NGPCR (e.g., by transfection or transduction of NGPCR DNA) can be used. Interaction of the test compound with, for example, a ECD of a NGPCR expressed by the host cell can be determined by comparison or competition with native ligand.

5.5.2. Assays for Intracellular Proteins that Interact with NGPCRs

Any method suitable for detecting protein-protein interactions may be employed for identifying transmembrane proteins or intracellular proteins that interact with a NGPCR. Among the traditional methods which may be employed are co-immunoprecipitation, crosslinking and co-purification through gradients or chromatographic columns of cell lysates or proteins obtained from cell lysates and a NGPCR to identify proteins in the lysate that interact with the NGPCR. For these assays, the NGPCR component used can be a full length NGPCR, a soluble derivative lacking the membrane-anchoring region (e.g., a truncated NGPCR in which a TM is deleted resulting in a truncated molecule containing a ECD fused to a CD), a peptide corresponding to a CD or a fusion protein containing a CD of a NGPCR. Once isolated, such an intracellular protein can be identified and can, in turn, be used, in conjunction with standard techniques, to identify proteins with which it interacts. For example, at least a portion of the amino acid sequence of an intracellular protein which interacts with a NGPCR can be ascertained using techniques well-known to those of skill in the art, such as via the Edman degradation technique. (See, e.g., Creighton, 1983, "Proteins: Structures and Molecular Principles", W.H. Freeman & Co., NY, pp.34–49). The amino acid sequence obtained may be used as a guide for the generation of oligonucleotide mixtures that can be used to screen for gene sequences encoding such intracellular proteins. Screening can be accomplished, for example, by standard hybridization or PCR techniques. Techniques for the generation of oligonucleotide mixtures and the screening are well-known. (See, e.g., Ausubel, supra, and PCR Protocols: A Guide to Methods and Applications, 1990, Innis, M. et al., eds. Academic Press, Inc., NY).

Additionally, methods may be employed which result in the simultaneous identification of genes which encode the transmembrane or intracellular proteins interacting with NGPCR. These methods include, for example, probing expression, libraries, in a manner similar to the well-known technique of antibody probing of λgt11 libraries, using labeled NGPCR protein, or an NGPCR polypeptide, peptide or fusion protein, e.g., an NGPCR polypeptide or NGPCR domain fused to a marker (e.g., an enzyme, fluor, luminescent protein, or dye), or an Ig-Fc domain.

One method that detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to a NGPCR nucleotide sequence encoding NGPCR, an NGPCR polypeptide, peptide or fusion protein, and the other plasmid consists of nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast Saccharomyces cerevisiae that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, a NGPCR may be used as the bait gene product. Total genomic or cDNA sequences are fused to the DNA encoding an activation domain. This library and a plasmid encoding a hybrid of a bait NGPCR gene product fused to the DNA-binding domain are cotransformed into a yeast reporter strain, and the resulting transformants are screened for those that express the reporter gene. For example, and not by way of limitation, a bait NGPCR gene sequence, such as the open reading frame of a NGPCR (or a domain of a NGPCR) can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait NGPCR gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait NGPCR gene-GAL4 fusion plasmid into a yeast strain which contains a lacZ gene driven by a promoter which contains GAL4 activation sequence. A cDNA encoded protein, fused to GAL4 transcriptional activation domain, that interacts with bait NGPCR gene product will reconstitute an active GAL4 protein and thereby drive expression of the HIS3 gene. Colonies which express HIS3 can be detected by their growth on petri dishes containing semi-solid agar based media lacking histidine. The cDNA can then be purified from these strains, and used to produce and isolate the bait NGPCR gene-interacting protein using techniques routinely practiced in the art.

5.5.3. Assays for Compounds that Interfere with NGPCR/Intracellular or NGPCR/Transmembrane Macromolecule Interaction The macromolecules that interact with the NGPCR are referred to, for purposes of this discussion, as "binding partners." These binding partners are likely to be involved in the NGPCR signal transduction pathway. Therefore, it is desirable to identify compounds that interfere with or disrupt the interaction of such binding partners which may be useful in regulating the activity of a NGPCR and controlling disorders associated with NGPCR activity. For example, given their expression pattern, the described NGPCRs are contemplated to be particularly useful in methods for identifying compounds useful in the therapeutic treatment of high or low blood pressure (and associated symptoms), kidney disorders, metabolic disorders, and cancer.

The basic principle of the assay systems used to identify compounds that interfere with the interaction between a NGPCR and its binding partner or partners involves preparing a reaction mixture containing NGPCR protein, polypeptide, peptide or fusion protein as described in Sections 5.5.1 and 5.5.2 above, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the NGPCR moiety and its binding partner. Control reaction mixtures are incubated without the test compound or with a placebo. The formation of any complexes between the NGPCR moiety and the binding partner is then detected. The formation of a complex in the control reaction, but not in the reaction mixture containing the test compound, indicates that the compound interferes with the interaction of the NGPCR and the interactive binding partner. Additionally, complex formation within reaction mixtures containing the test compound and normal NGPCR protein may also be compared to complex formation within reaction mixtures containing the test compound and a mutant NGPCR. This comparison may be important in those cases wherein it is desirable to identify compounds that specifically disrupt interactions of mutant, or mutated, NGPCRs but not normal NGPCRs.

The assay for compounds that interfere with the interaction of a NGPCR and its binding partners can be conducted in a heterogeneous or homogeneous format. Heterogeneous assays involve anchoring either the NGPCR moiety product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction by competition can be identified by conducting the reaction in the presence of the test substance; i.e., by adding the test substance to the reaction mixture prior to, or simultaneously with, a NGPCR moiety and interactive binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either a NGPCR moiety or an interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the NGPCR gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt pre-formed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of a NGPCR moiety and an interactive binding partner is prepared in which either the NGPCR or its binding partners is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt NGPCR/intracellular binding partner interaction can be identified.

In a particular embodiment, a NGPCR fusion can be prepared for immobilization. For example, a NGPCR or a peptide fragment, e.g., corresponding to a CD, can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art and described above, in Section 5.3. This antibody can be labeled with the radioactive isotope $^{125}$I, for example, by methods routinely practiced in the art. In a heterogeneous assay, e.g., the GST-NGPCR fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between a NGPCR gene product and the interactive binding partner can be detected by measuring the amount of radioactivity that remains associated with the glutathione-agarose beads. A successful inhibition of the interaction by the test compound will result in a decrease in measured radioactivity.

Alternatively, the GST-NGPCR fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the NGPCR/binding partner interaction can be detected by adding the labeled antibody and measuring the radioactivity associated with the beads.

In another embodiment of the invention, these same techniques can be employed using peptide fragments that correspond to the binding domains of a NGPCR and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensatory mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a relatively short, labeled peptide comprising the binding domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, a NGPCR gene product can be anchored to a solid material as described, above, by making a GST-NGPCR fusion protein and allowing it to bind to glutathione agarose beads. The interactive binding partner can be labeled with a radioactive isotope, such as $^{35}$S, and cleaved with a proteolytic enzyme such as trypsin. Cleavage products can then be added to the anchored GST-NGPCR fusion protein and allowed to bind. After washing away unbound peptides, labeled bound material, representing the intracellular binding partner binding domain, can be eluted, purified, and analyzed for amino acid sequence by well-known methods. Peptides so identified can be produced synthetically or fused to appropriate facilitative proteins using recombinant DNA technology.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims. All referenced publications, patents, and patent applications are herein incorporated by reference.

What is claimed is:

1. An isolated nucleic acid molecule comprising a NGPCR nucleotide sequence selected from the group consisting of SEQ ID NOS: 1 and 3.

2. An isolated nucleic acid molecule comprising a nucleotide sequence that:
   (a) encodes the amino acid sequence shown in SEQ ID NO:2; and
   (b) hybridizes under highly stringent conditions to the nucleotide sequence of SEQ ID NO:1 or the full-length complement thereof.

3. An isolated nucleic acid molecule according to claim 1 wherein said molecule is a cDNA.

4. An isolated nucleic acid molecule comprising a nucleotide sequence that encodes the amino acid sequence shown in SEQ ID NO:2.

5. An isolated nucleic acid molecule comprising the NGPCR nucleotide sequence described in SEQ ID NO:3.

6. An isolated nucleic acid molecule comprising a nucleotide sequence that encodes the amino acid sequence shown in SEQ ID NO:4.

* * * * *

UNITED STATES PATENT AND TRADEMARK OFFICE
CERTIFICATE OF CORRECTION

PATENT NO.    : 6,570,003 B1
DATED         : May 27, 2003
INVENTOR(S)   : Hu et al.

It is certified that error appears in the above-identified patent and that said Letters Patent is hereby corrected as shown below:

<u>Title page,</u>
Item [73], Assignee, should read as follows:
-- [73] Assignee:   Lexicon Genetics Incorporated --.

Signed and Sealed this

Second Day of December, 2003

JAMES E. ROGAN
*Director of the United States Patent and Trademark Office*

SEQUENCE LISTING

<160> NUMBER OF SEQ ID NOS: 5

<210> SEQ ID NO 1
<211> LENGTH: 3747
<212> TYPE: DNA
<213> ORGANISM: homo sapiens -continued

```
<400> SEQUENCE: 1
atgcaagctg gccccaccag tggtgaaagc ggatgcccag cacataacag caccttgtcc      60
tgtctgtgtc ctctctgtct cttcaggctc ttgagcaata acaagatcac ggggctccgc     120
aatggctcct tcctgggact gtcactgctg gagaagctgg acctgaggaa caacatcatc     180
agcacagtgc agccgggcgc cttcctgggc ctggggagc tgaagcgttt agatctctcc      240
aacaaccgga ttgctgtct cacctccgag accttccagg gcctcccag gcttctccga       300 ctaaacatat ctggaaacat cttctccagt ctgcaacctg gggtctttga tgagctgcca     360
gcccttaagg ttgtggactt gggcaccgag ttcctgacct gtgactgcca cctgcgctgg     420
ctgctgccct gggcccagaa tcgctccctg cagctgtcgg aacacacgct ctgtgcttac     480
cccagtgccc tgcatgctca ggccctgggc agcctccagg aggcccagct gctgctgcgag    540 ggggccctgg agctgcacac acaccacctc atcccgtccc tacgccaagt ggtgttccag     600
ggggatcggc tgcccttcca gtgctctgcc agctacctgg gcaacgacac ccgcatccgc     660
tggtaccaca accgagcccc tgtggagggt gatgagcagg cggcatcct cctggccgag      720 agcctcatcc acgactgcac cttcatcacc agtgagctga cgctgtctca catcggcgtg     780
tgggcctcag gcgagtggga gtgcaccgtg tccatggccc aaggcaacgc cagcaagaag     840
gtggagatcg tggtgctgga gacctctgcc tcctactgcc ccgccgagcg tgttgccaac     900
aaccgcgggg acttcaggtg ccccgaact ctggctggca tcacagccta ccagtcctgc     960
ctgcagtatc ccttcacctc agtgccctg gcgcggggtg ccccgggcac ccgagcctcc    1020
cgccggtgtg accgtgccgg ccgctgggag ccaggggact actcccactg tctctacacc    1080
aacgacatca ccagggtgct gtacaccttc gtgctgatgc ccatcaatgc ctccaatgcg    1140
ctgaccctgg ctcaccagct gcgcgtgtac acagccgagg ccgctagctt ttcagacatg    1200
atggatgtag tctatgtggc tcagatgatc cagaaatttt tgggttatgt cgaccagatc    1260
aaagagctgg tagaggtgat ggtggacatg ccagcaacc tgatgctggt ggacgagcac     1320
ctgctgtggc tggcccagcg cgaggacaag gcctgcagcc gcatcgtggg tgccctggag    1380
cgcattgggg gggccgccct cagcccccat gcccagcaca tctcagtgaa tgcgaggaac    1440
gtggcattgg aggcctacct catcaagccg cacagctacg tgggcctgac ctgcacagcc    1500
ttccagagga gggagggagg ggtgccgggc acacggccag aagccctggg ccagaacccc    1560
ccacctgagc ccgagccccc agctgaccag cagctccgct tccgctgcac caccgggagg    1620
cccaatgttt ctctgtcgtc cttccacatc aagaacagcg tggccctggc ctccatccag    1680 ctgccccga gtctattctc atcccttccg gctgccctgg ctccccggt gcccccagac      1740 tgcaccctgc aactgctcgt cttccgaaat ggccgcctct tccacagcca cagcaacacc    1800
tcccgccctg gagctgctgg gcctggcaag aggcgtggcg tggccacccc cgtcatcttc    1860
gcaggaacca gtggctgtgg cgtgggaaac ctgacagagc cagtggccgt ttcgctgcgg    1920
cactgggctg agggagccga acctgtggcc gcttggtgga gcaggagggg gcccggggag    1980
gctgggggct ggacctcgga gggctgccag ctccgctcca gccagcccaa tgtcagcgcc    2040
ctgcactgcc agcacttggg caatgtggcc gtgctcatgg agctgagcgc ctttcccagg    2100
gaggtggggg gcgccggggc agggctgcac cccgtggtat accctgcac ggccttgctg     2160 ctgctctgcc tcttcgccac catcatcacc tacatcctca accacagctc catccgtgtg    2220
tcccggaaag gctggcacat gctgctgaac ttgtgcttcc acatagccat gacctctgct    2280
gtctttgcgg ggggcatcac actcaccaac taccagatgg tctgccaggc ggtgggcatc    2340
```

```
accctgcact actcctccct atccacgctg ctctggatgg gcgtgaaggc gcgagtgctc   2400
cataaggagc tcacctggag ggcacccct  ccgcaagaag gggacccgc  tctgcctact   2460
cccagtccta tgctccgctg ctggctggtg tggcgtccaa gccttggcgc cttctacatc   2520
cctgtggctt tgattctgct catcacctgg atctatttcc tgtgcgccgg gctacgctta   2580
cggggtcctc tggcacagaa ccccaaggcg ggcaacagca gggcctccct ggaggcaggg   2640
gaggagctga ggggttccac caggctcagg ggcagcggcc ccctcctgag tgactcaggt   2700
tcccttcttg ctactgggag cgcgcgagtg gggacgcccg gccccccgga ggatggtgac   2760
agcctctatt ctccgggagt ccagctaggg gcgctggtga ccacgcactt cctgtacttg   2820
gccatgtggg cctgcgggc  tctggcagtg tcccagcgct ggctgccccg ggtggtgtgc   2880
agctgcttgt acgggtggc  agcctccgcc ctgggcctct tcgtcttcac tcaccactgt   2940
gccaggcgga gggacgtgag agcctcgtgg cgcgcctgct gccccctgc  ctctcccgcg   3000
gccccccatg cccgccccg  ggccctgccc gccgccgcag aggacggttc cccggtgttc   3060
ggggaggggc cccctcccct caagtcctcc ccaagcggca gcagcggcca tccgctggct   3120
ctgggcccct gcaagctcac caacctgcag ctggcccaga gtcaggtgtg cgaggcgggg   3180
gcggcggccg gcggggaagg agagccggag ccggcgggca cccggggaaa cctcgcccac   3240
cgccacccca acaacgtgca ccacgggcgt cgggcgcaca agagccgggc caagggacac   3300
cgcgcggggg aggcctgcgg caagaaccgg ctcaaggccc tgcgcggggg gcgggcgggg   3360
gcgctggagc tgctgtccag cgagagcggt agtctgcaca acagccccac cgacagctac   3420
ctgggcagca gccgcaacag cccgggcgcc ggcctgcagc tggaaggcga gcccatgctc   3480
acgccgtccg agggcagcga caccagcgcc gcgccgcttt ctgaggcggg ccgggcaggc   3540
cagcgccgca gcgccagccg cgacagtctc aagggcggcg gcgcgctgga aggagagagc   3600
catcgccgct cgtacccgct caacgccgcc agcctaaacg gcgcccccaa gggggcaag   3660
tacgacgacg tcacctgat  gggcgcggag gtagccagcg gcggctgcat gaagaccgga   3720
ctctggaaga gcgaaactac cgtctaa                                      3747
```

<210> SEQ ID NO 2
<211> LENGTH: 1248
<212> TYPE: PRT
<213> ORGANISM: homo sapiens

<400> SEQUENCE: 2

```
Met Gln Ala Gly Pro Thr Ser Gly Glu Ser Gly Cys Pro Ala His Asn
 1               5                  10                  15

Ser Thr Leu Ser Cys Leu Cys Pro Leu Cys Leu Phe Arg Leu Leu Ser
            20                  25                  30

Asn Asn Lys Ile Thr Gly Leu Arg Asn Gly Ser Phe Leu Gly Leu Ser
        35                  40                  45

Leu Leu Glu Lys Leu Asp Leu Arg Asn Asn Ile Ile Ser Thr Val Gln
    50                  55                  60

Pro Gly Ala Phe Leu Gly Leu Gly Glu Leu Lys Arg Leu Asp Leu Ser
65                  70                  75                  80

Asn Asn Arg Ile Gly Cys Leu Ser Glu Thr Phe Gln Gly Leu Pro
            85                  90                  95

Arg Leu Leu Arg Leu Asn Ile Ser Gly Asn Ile Phe Ser Ser Leu Gln
           100                 105                 110

Pro Gly Val Phe Asp Glu Leu Pro Ala Leu Lys Val Val Asp Leu Gly
```

-continued

```
            115                 120                 125
Thr Glu Phe Leu Thr Cys Asp Cys His Leu Arg Trp Leu Leu Pro Trp
130                 135                 140
Ala Gln Asn Arg Ser Leu Gln Leu Ser Glu His Thr Leu Cys Ala Tyr
145                 150                 155                 160
Pro Ser Ala Leu His Ala Gln Ala Leu Gly Ser Leu Gln Glu Ala Gln
                165                 170                 175
Leu Cys Cys Glu Gly Ala Leu Glu Leu His Thr His His Leu Ile Pro
            180                 185                 190
Ser Leu Arg Gln Val Val Phe Gln Gly Asp Arg Leu Pro Phe Gln Cys
        195                 200                 205
Ser Ala Ser Tyr Leu Gly Asn Asp Thr Arg Ile Arg Trp Tyr His Asn
210                 215                 220
Arg Ala Pro Val Glu Gly Asp Glu Gln Ala Gly Ile Leu Leu Ala Glu
225                 230                 235                 240
Ser Leu Ile His Asp Cys Thr Phe Ile Thr Ser Glu Leu Thr Leu Ser
                245                 250                 255
His Ile Gly Val Trp Ala Ser Gly Glu Trp Glu Cys Thr Val Ser Met
            260                 265                 270
Ala Gln Gly Asn Ala Ser Lys Lys Val Glu Ile Val Val Leu Glu Thr
        275                 280                 285
Ser Ala Ser Tyr Cys Pro Ala Glu Arg Val Ala Asn Asn Arg Gly Asp
290                 295                 300
Phe Arg Trp Pro Arg Thr Leu Ala Gly Ile Thr Ala Tyr Gln Ser Cys
305                 310                 315                 320
Leu Gln Tyr Pro Phe Thr Ser Val Pro Leu Gly Gly Gly Ala Pro Gly
                325                 330                 335
Thr Arg Ala Ser Arg Arg Cys Asp Arg Ala Gly Arg Trp Glu Pro Gly
            340                 345                 350
Asp Tyr Ser His Cys Leu Tyr Thr Asn Asp Ile Thr Arg Val Leu Tyr
        355                 360                 365
Thr Phe Val Leu Met Pro Ile Asn Ala Ser Asn Ala Leu Thr Leu Ala
370                 375                 380
His Gln Leu Arg Val Tyr Thr Ala Glu Ala Ala Ser Phe Ser Asp Met
385                 390                 395                 400
Met Asp Val Val Tyr Val Ala Gln Met Ile Gln Lys Phe Leu Gly Tyr
                405                 410                 415
Val Asp Gln Ile Lys Glu Leu Val Glu Val Met Val Asp Met Ala Ser
            420                 425                 430
Asn Leu Met Leu Val Asp Glu His Leu Leu Trp Leu Ala Gln Arg Glu
        435                 440                 445
Asp Lys Ala Cys Ser Arg Ile Val Gly Ala Leu Glu Arg Ile Gly Gly
450                 455                 460
Ala Ala Leu Ser Pro His Ala Gln His Ile Ser Val Asn Ala Arg Asn
465                 470                 475                 480
Val Ala Leu Glu Ala Tyr Leu Ile Lys Pro His Ser Tyr Val Gly Leu
                485                 490                 495
Thr Cys Thr Ala Phe Gln Arg Arg Glu Gly Gly Val Pro Gly Thr Arg
            500                 505                 510
Pro Gly Ser Pro Gly Gln Asn Pro Pro Glu Pro Glu Pro Ala
        515                 520                 525
Asp Gln Gln Leu Arg Phe Arg Cys Thr Thr Gly Arg Pro Asn Val Ser
530                 535                 540
```

-continued

```
Leu Ser Ser Phe His Ile Lys Asn Ser Val Ala Leu Ala Ser Ile Gln
545                 550                 555                 560

Leu Pro Pro Ser Leu Phe Ser Ser Leu Pro Ala Ala Leu Ala Pro Pro
                565                 570                 575

Val Pro Pro Asp Cys Thr Leu Gln Leu Leu Val Phe Arg Asn Gly Arg
            580                 585                 590

Leu Phe His Ser His Ser Asn Thr Ser Arg Pro Gly Ala Ala Gly Pro
        595                 600                 605

Gly Lys Arg Arg Gly Val Ala Thr Pro Val Ile Phe Ala Gly Thr Ser
610                 615                 620

Gly Cys Gly Val Gly Asn Leu Thr Glu Pro Val Ala Val Ser Leu Arg
625                 630                 635                 640

His Trp Ala Glu Gly Ala Glu Pro Val Ala Ala Trp Trp Ser Gln Glu
                645                 650                 655

Gly Pro Gly Glu Ala Gly Gly Trp Thr Ser Glu Gly Cys Gln Leu Arg
                660                 665                 670

Ser Ser Gln Pro Asn Val Ser Ala Leu His Cys Gln His Leu Gly Asn
            675                 680                 685

Val Ala Val Leu Met Glu Leu Ser Ala Phe Pro Arg Glu Val Gly Gly
        690                 695                 700

Ala Gly Ala Gly Leu His Pro Val Val Tyr Pro Cys Thr Ala Leu Leu
705                 710                 715                 720

Leu Leu Cys Leu Phe Ala Thr Ile Ile Thr Tyr Ile Leu Asn His Ser
                725                 730                 735

Ser Ile Arg Val Ser Arg Lys Gly Trp His Met Leu Leu Asn Leu Cys
            740                 745                 750

Phe His Ile Ala Met Thr Ser Ala Val Phe Ala Gly Gly Ile Thr Leu
        755                 760                 765

Thr Asn Tyr Gln Met Val Cys Gln Ala Val Gly Ile Thr Leu His Tyr
    770                 775                 780

Ser Ser Leu Ser Thr Leu Leu Trp Met Gly Val Lys Ala Arg Val Leu
785                 790                 795                 800

His Lys Glu Leu Thr Trp Arg Ala Pro Pro Gln Glu Gly Asp Pro
                805                 810                 815

Ala Leu Pro Thr Pro Ser Pro Met Leu Arg Cys Trp Leu Val Trp Arg
            820                 825                 830

Pro Ser Leu Gly Ala Phe Tyr Ile Pro Val Ala Leu Ile Leu Leu Ile
        835                 840                 845

Thr Trp Ile Tyr Phe Leu Cys Ala Gly Leu Arg Leu Arg Gly Pro Leu
850                 855                 860

Ala Gln Asn Pro Lys Ala Gly Asn Ser Arg Ala Ser Leu Glu Ala Gly
865                 870                 875                 880

Glu Glu Leu Arg Gly Ser Thr Arg Leu Arg Gly Ser Gly Pro Leu Leu
                885                 890                 895

Ser Asp Ser Gly Ser Leu Leu Ala Thr Gly Ser Ala Arg Val Gly Thr
            900                 905                 910

Pro Gly Pro Pro Glu Asp Gly Asp Ser Leu Tyr Ser Pro Gly Val Gln
        915                 920                 925

Leu Gly Ala Leu Val Thr Thr His Phe Leu Tyr Leu Ala Met Trp Ala
    930                 935                 940

Cys Gly Ala Leu Ala Val Ser Gln Arg Trp Leu Pro Arg Val Val Cys
945                 950                 955                 960
```

-continued

Ser Cys Leu Tyr Gly Val Ala Ala Ser Ala Leu Gly Leu Phe Val Phe
            965                 970                 975

Thr His His Cys Ala Arg Arg Arg Asp Val Arg Ala Ser Trp Arg Ala
            980                 985                 990

Cys Cys Pro Pro Ala Ser Pro Ala Ala Pro His Ala Pro Pro Arg Ala
            995                1000                1005

Leu Pro Ala Ala Ala Glu Asp Gly Ser Pro Val Phe Gly Glu Gly Pro
           1010                1015                1020

Pro Ser Leu Lys Ser Ser Pro Ser Gly Ser Gly His Pro Leu Ala
1025                1030                1035                1040

Leu Gly Pro Cys Lys Leu Thr Asn Leu Gln Leu Ala Gln Ser Gln Val
           1045                1050                1055

Cys Glu Ala Gly Ala Ala Ala Gly Gly Glu Gly Glu Pro Glu Pro Ala
           1060                1065                1070

Gly Thr Arg Gly Asn Leu Ala His Arg His Pro Asn Asn Val His His
           1075                1080                1085

Gly Arg Arg Ala His Lys Ser Arg Ala Lys Gly His Arg Ala Gly Glu
           1090                1095                1100

Ala Cys Gly Lys Asn Arg Leu Lys Ala Leu Arg Gly Gly Ala Ala Gly
1105                1110                1115                1120

Ala Leu Glu Leu Leu Ser Ser Glu Ser Gly Ser Leu His Asn Ser Pro
           1125                1130                1135

Thr Asp Ser Tyr Leu Gly Ser Ser Arg Asn Ser Pro Gly Ala Gly Leu
           1140                1145                1150

Gln Leu Glu Gly Glu Pro Met Leu Thr Pro Ser Glu Gly Ser Asp Thr
           1155                1160                1165

Ser Ala Ala Pro Leu Ser Glu Ala Gly Arg Ala Gly Gln Arg Arg Ser
           1170                1175                1180

Ala Ser Arg Asp Ser Leu Lys Gly Gly Gly Ala Leu Glu Lys Glu Ser
1185                1190                1195                1200

His Arg Arg Ser Tyr Pro Leu Asn Ala Ala Ser Leu Asn Gly Ala Pro
           1205                1210                1215

Lys Gly Gly Lys Tyr Asp Asp Val Thr Leu Met Gly Ala Glu Val Ala
           1220                1225                1230

Ser Gly Gly Cys Met Lys Thr Gly Leu Trp Lys Ser Glu Thr Thr Val
           1235                1240                1245

<210> SEQ ID NO 3
<211> LENGTH: 3837
<212> TYPE: DNA
<213> ORGANISM: homo sapiens

<400> SEQUENCE: 3
atgcaagctg gccccaccag tggtgaaagc ggatgcccag cacataacag caccttgtcc      60
tgtctgtgtc ctctctgtct cttcaggctc ttgagcaata acaagatcac ggggctccgc     120
aatggctcct tcctgggact gtcactgctg gagaagctgg acctgaggaa caacatcatc     180
agcacagtgc agccgggcgc cttcctgggc ctggggagc tgaagcgttt agatctctcc      240
aacaaccgga ttggctgtct cacctccgag accttccagg gcctccccag gcttctccga     300
ctaaacatat ctggaaacat cttctccagt ctgcaacctg ggtctttga tgagctgcca      360 gcccttaagg ttgtggactt gggcaccgag ttcctgacct gtgactgcca cctgcgctgg     420
ctgctgccct gggcccagaa tcgctccctg cagtgtcgg aacacacgct ctgtgcttac     480
cccagtgccc tgcatgctca ggccctgggc agcctccagg aggcccagct ctgctgcgag     540

-continued

```
ggggccctgg agctgcacac acaccacctc atcccgtccc tacgccaagt ggtgttccag      600 gggatcggc  tgcccttcca gtgctctgcc agctacctgg gcaacgacac ccgcatccgc      660
tggtaccaca accgagcccc tgtggagggt gatgagcagg cgggcatcct cctggccgag      720
agcctcatcc acgactgcac cttcatcacc agtgagctga cgctgtctca catcggcgtg      780
tgggcctcag gcgagtggga gtgcaccgtg tccatggccc aaggcaacgc cagcaagaag      840
gtggagatcg tggtgctgga gacctctgcc tcctactgcc ccgccagcg tgttgccaac      900 aaccgcgggg acttcaggtg gccccgaact ctggctggca tcacagccta ccagtcctgc      960
ctgcagtatc ccttcacctc agtgcccctg gcgggggtg ccccgggcac ccgagcctcc     1020
cgccggtgtg accgtgccgg ccgctgggag ccaggggact actcccactg tctctacacc     1080
aacgacatca ccagggtgct gtacaccttc gtgctgatgc ccatcaatgc ctccaatgcg     1140
ctgaccctgg ctcaccagct cgcgtgtac acagccgagg ccgctagctt ttcagacatg     1200
atggatgtag tctatgtggc tcagatgatc cagaaatttt tgggttatgt cgaccagatc     1260
aaagagctgg tagaggtgat ggtggacatg ccagcaacc tgatgctggt ggacgagcac     1320
ctgctgtggc tggcccagcg cgaggacaag gcctgcagcc gcatcgtggg tgccctggag     1380
cgcattgggg gggccgccct cagcccccat gcccagcaca tctcagtgaa tgcgaggaac     1440
gtggcattgg aggcctacct catcaagccg cacagctacg tgggcctgac ctgcacagcc     1500
ttccagagga gggagggagg ggtgccgggc acacggccag gaagccctgg ccagaacccc     1560
ccacctgagc ccgagcccc  agctgaccag cagctccgct tccgctgcac caccgggagg     1620
cccaatgttt tctctgtcgtc cttccacatc aagaacagcg tggccctggc ctccatccag     1680
ctgcccccga gtctattctc atcccttccg gctgccctgg ctcccccggt gccccagac     1740 tgcaccctgc aactgctcgt cttccgaaat ggccgcctct tccacagcca cagcaacacc     1800
tcccgccctg gagctgctgg gcctggcaag aggcgtggcg tggccacccc cgtcatcttc     1860
gcaggaacca gtggctgtgg cgtgggaaac ctgacagagc cagtggccgt ttcgctgcgg     1920
cactgggctg agggagccga acctgtggcc gcttggtgga gccaggaggg gcccggggag     1980
gctgggggct ggaccctcgga gggctgccag ctccgctcca gccagcccaa tgtcagcgcc     2040
ctgcactgcc agcacttggg caatgtggcc gtgctcatgg agctgagcgc ctttcccagg     2100
gaggtggggg gcgccggggc agggctgcac cccgtggtat accctgcac ggccttgctg      2160 ctgctctgcc tcttcgccac catcatcacc tacatcctca accacagctc catccgtgtg     2220
tcccggaaag gctggcacat gctgctgaac ttgtgcttcc acatagccat gacctctgct     2280
gtctttgcgg ggggcatcac actcaccaac taccagatgg tctgccaggc ggtgggcatc     2340
accctgcact actcctccct atccacgctg ctctggatgg gcgtgaaggc gcgagtgctc     2400
cataaggagc tcacctggag ggcaccccct ccgcaagaag ggaccccgc tctgcctact     2460 cccagtccta tgctccggtt ctatttgatc gctggaggga ttccactcat tatctgtggc     2520
atcacagctg cagtcaacat ccacaactac cgggaccaca gccctactg ctggctggtg     2580 tggcgtccaa gccttggcgc cttctacatc cctgtggctt tgattctgct catcacctgg     2640
atctatttcc tgtgcgccgg gctacgctta cggggtcctc tggcacagaa ccccaaggcg     2700
ggcaacagca gggcctccct ggaggcaggg gaggagctga ggggttccac caggctcagg     2760
ggcagcggcc cctcctgag tgactcaggt tcccttcttg ctactgggag cgcgcgagtg     2820 ggacgcccg  ggcccccgga ggatggtgac agcctctatt ctccgggagt ccagctaggg     2880
```

-continued

```
gcgctggtga ccacgcactt cctgtacttg gccatgtggg cctgcggggc tctggcagtg     2940
tcccagcgct ggctgccccg ggtggtgtgc agctgcttgt acggggtggc agcctccgcc     3000
ctgggcctct tcgtcttcac tcaccactgt gccaggcgga gggacgtgag agcctcgtgg     3060
cgcgcctgct gccccctgc ctctcccgcg ccccccatg cccgccccg ggccctgccc        3120 gccgccgcag aggacggttc cccggtgttc ggggagggc cccctccct caagtcctcc       3180 ccaagcggca gcagcggcca tccgctggct ctgggcccct gcaagctcac caacctgcag     3240
ctggcccaga gtcaggtgtg cgaggcgggg cggcggccg gcggggaagg agagccggag      3300
ccggcgggca cccggggaaa cctcgcccac cgccacccca acaacgtgca ccacgggcgt     3360
cgggcgcaca agagccgggc caagggacac cgcgcggggg aggcctgcgg caagaaccgg     3420
ctcaaggccc tgcgcggggg cgcggcgggg cgctggagc tgctgtccag cgagagcggt      3480
agtctgcaca acagccccac cgacagctac ctgggcagca gccgcaacag cccgggcgcc     3540
ggcctgcagc tggaaggcga gcccatgctc acgccgtccg agggcagcga caccagcgcc     3600
gcgccgcttt ctgaggcggg ccgggcaggc cagcgccgca cgccagccg cgacagtctc      3660 aagggcggcg gcgcgctgga gaaggagagc catcgccgct cgtacccgct caacgccgcc     3720
agcctaaacg gcgcccccaa gggggggcaag tacgacgacg tcaccctgat gggcgcggag     3780
gtagccagcg gcggctgcat gaagaccgga ctctggaaga gcgaaactac cgtctaa       3837
```

<210> SEQ ID NO 4
<211> LENGTH: 1278
<212> TYPE: PRT
<213> ORGANISM: homo sapiens

<400> SEQUENCE: 4

```
Met Gln Ala Gly Pro Thr Ser Gly Glu Ser Gly Cys Pro Ala His Asn
  1               5                  10                  15

Ser Thr Leu Ser Cys Leu Cys Pro Leu Cys Leu Phe Arg Leu Leu Ser
             20                  25                  30

Asn Asn Lys Ile Thr Gly Leu Arg Asn Gly Ser Phe Leu Gly Leu Ser
         35                  40                  45

Leu Leu Glu Lys Leu Asp Leu Arg Asn Asn Ile Ile Ser Thr Val Gln
     50                  55                  60

Pro Gly Ala Phe Leu Gly Leu Gly Glu Leu Lys Arg Leu Asp Leu Ser
 65                  70                  75                  80

Asn Asn Arg Ile Gly Cys Leu Thr Ser Glu Thr Phe Gln Gly Leu Pro
                 85                  90                  95

Arg Leu Leu Arg Leu Asn Ile Ser Gly Asn Ile Phe Ser Ser Leu Gln
            100                 105                 110

Pro Gly Val Phe Asp Glu Leu Pro Ala Leu Lys Val Val Asp Leu Gly
        115                 120                 125

Thr Glu Phe Leu Thr Cys Asp Cys His Leu Arg Trp Leu Leu Pro Trp
    130                 135                 140

Ala Gln Asn Arg Ser Leu Gln Leu Ser Glu His Thr Leu Cys Ala Tyr
145                 150                 155                 160

Pro Ser Ala Leu His Ala Gln Ala Leu Gly Ser Leu Gln Glu Ala Gln
                165                 170                 175

Leu Cys Cys Glu Gly Ala Leu Glu Leu His Thr His Leu Ile Pro
            180                 185                 190

Ser Leu Arg Gln Val Val Phe Gln Gly Asp Arg Leu Pro Phe Gln Cys
        195                 200                 205
```

```
Ser Ala Ser Tyr Leu Gly Asn Asp Thr Arg Ile Arg Trp Tyr His Asn
    210                 215                 220
Arg Ala Pro Val Glu Gly Asp Glu Gln Ala Gly Ile Leu Leu Ala Glu
225                 230                 235                 240
Ser Leu Ile His Asp Cys Thr Phe Ile Thr Ser Glu Leu Thr Leu Ser
                245                 250                 255
His Ile Gly Val Trp Ala Ser Gly Glu Trp Glu Cys Thr Val Ser Met
            260                 265                 270
Ala Gln Gly Asn Ala Ser Lys Lys Val Glu Ile Val Val Leu Glu Thr
        275                 280                 285
Ser Ala Ser Tyr Cys Pro Ala Glu Arg Val Ala Asn Asn Arg Gly Asp
    290                 295                 300
Phe Arg Trp Pro Arg Thr Leu Ala Gly Ile Thr Ala Tyr Gln Ser Cys
305                 310                 315                 320
Leu Gln Tyr Pro Phe Thr Ser Val Pro Leu Gly Gly Ala Pro Gly
                325                 330                 335
Thr Arg Ala Ser Arg Arg Cys Asp Arg Ala Gly Arg Trp Glu Pro Gly
                340                 345                 350
Asp Tyr Ser His Cys Leu Tyr Thr Asn Asp Ile Thr Arg Val Leu Tyr
            355                 360                 365
Thr Phe Val Leu Met Pro Ile Asn Ala Ser Asn Ala Leu Thr Leu Ala
        370                 375                 380
His Gln Leu Arg Val Tyr Thr Ala Glu Ala Ala Ser Phe Ser Asp Met
385                 390                 395                 400
Met Asp Val Val Tyr Val Ala Gln Met Ile Gln Lys Phe Leu Gly Tyr
                405                 410                 415
Val Asp Gln Ile Lys Glu Leu Val Glu Val Met Val Asp Met Ala Ser
            420                 425                 430
Asn Leu Met Leu Val Asp Glu His Leu Leu Trp Leu Ala Gln Arg Glu
        435                 440                 445
Asp Lys Ala Cys Ser Arg Ile Val Gly Ala Leu Glu Arg Ile Gly Gly
    450                 455                 460
Ala Ala Leu Ser Pro His Ala Gln His Ile Ser Val Asn Ala Arg Asn
465                 470                 475                 480
Val Ala Leu Glu Ala Tyr Leu Ile Lys Pro His Ser Tyr Val Gly Leu
                485                 490                 495
Thr Cys Thr Ala Phe Gln Arg Arg Glu Gly Gly Val Pro Gly Thr Arg
            500                 505                 510
Pro Gly Ser Pro Gly Gln Asn Pro Pro Glu Pro Glu Pro Pro Ala
        515                 520                 525
Asp Gln Gln Leu Arg Phe Arg Cys Thr Thr Gly Arg Pro Asn Val Ser
    530                 535                 540
Leu Ser Ser Phe His Ile Lys Asn Ser Val Ala Leu Ala Ser Ile Gln
545                 550                 555                 560
Leu Pro Pro Ser Leu Phe Ser Ser Leu Pro Ala Ala Leu Ala Pro Pro
                565                 570                 575
Val Pro Pro Asp Cys Thr Leu Gln Leu Leu Val Phe Arg Asn Gly Arg
            580                 585                 590
Leu Phe His Ser His Ser Asn Thr Ser Arg Pro Gly Ala Ala Gly Pro
        595                 600                 605
Gly Lys Arg Arg Gly Val Ala Thr Pro Val Ile Phe Ala Gly Thr Ser
    610                 615                 620
Gly Cys Gly Val Gly Asn Leu Thr Glu Pro Val Ala Val Ser Leu Arg
```

```
625              630              635              640

His Trp Ala Glu Gly Ala Glu Pro Val Ala Ala Trp Trp Ser Gln Glu
                    645              650              655

Gly Pro Gly Glu Ala Gly Gly Trp Thr Ser Glu Gly Cys Gln Leu Arg
                660              665              670

Ser Ser Gln Pro Asn Val Ser Ala Leu His Cys Gln His Leu Gly Asn
            675              680              685

Val Ala Val Leu Met Glu Leu Ser Ala Phe Pro Arg Glu Val Gly Gly
        690              695              700

Ala Gly Ala Gly Leu His Pro Val Val Tyr Pro Cys Thr Ala Leu Leu
705              710              715              720

Leu Leu Cys Leu Phe Ala Thr Ile Ile Thr Tyr Ile Leu Asn His Ser
                725              730              735

Ser Ile Arg Val Ser Arg Lys Gly Trp His Met Leu Asn Leu Cys
                740              745              750

Phe His Ile Ala Met Thr Ser Ala Val Phe Ala Gly Ile Thr Leu
                755              760              765

Thr Asn Tyr Gln Met Val Cys Gln Ala Val Gly Ile Thr Leu His Tyr
    770              775              780

Ser Ser Leu Ser Thr Leu Leu Trp Met Gly Val Lys Ala Arg Val Leu
785              790              795              800

His Lys Glu Leu Thr Trp Arg Ala Pro Pro Gln Glu Gly Asp Pro
                805              810              815

Ala Leu Pro Thr Pro Ser Pro Met Leu Arg Phe Tyr Leu Ile Ala Gly
                820              825              830

Gly Ile Pro Leu Ile Ile Cys Gly Ile Thr Ala Ala Val Asn Ile His
            835              840              845

Asn Tyr Arg Asp His Ser Pro Tyr Cys Trp Leu Val Trp Arg Pro Ser
850              855              860

Leu Gly Ala Phe Tyr Ile Pro Val Ala Leu Ile Leu Ile Thr Trp
865              870              875              880

Ile Tyr Phe Leu Cys Ala Gly Leu Arg Leu Arg Gly Pro Leu Ala Gln
                885              890              895

Asn Pro Lys Ala Gly Asn Ser Arg Ala Ser Leu Glu Ala Gly Glu Glu
                900              905              910

Leu Arg Gly Ser Thr Arg Leu Arg Gly Ser Gly Pro Leu Leu Ser Asp
            915              920              925

Ser Gly Ser Leu Leu Ala Thr Gly Ser Ala Arg Val Gly Thr Pro Gly
930              935              940

Pro Pro Glu Asp Gly Asp Ser Leu Tyr Ser Pro Gly Val Gln Leu Gly
945              950              955              960

Ala Leu Val Thr Thr His Phe Leu Tyr Leu Ala Met Trp Ala Cys Gly
                965              970              975

Ala Leu Ala Val Ser Gln Arg Trp Leu Pro Arg Val Val Cys Ser Cys
            980              985              990

Leu Tyr Gly Val Ala Ala Ser Ala Leu Gly Leu Phe Val Phe Thr His
                995              1000             1005

His Cys Ala Arg Arg Arg Asp Val Arg Ala Ser Trp Arg Ala Cys Cys
    1010             1015             1020

Pro Pro Ala Ser Pro Ala Ala Pro His Ala Pro Pro Arg Ala Leu Pro
1025             1030             1035             1040

Ala Ala Ala Glu Asp Gly Ser Pro Val Phe Gly Glu Gly Pro Pro Ser
                1045             1050             1055
```

```
Leu Lys Ser Ser Pro Ser Gly Ser Ser Gly His Pro Leu Ala Leu Gly
        1060                1065                1070

Pro Cys Lys Leu Thr Asn Leu Gln Leu Ala Gln Ser Gln Val Cys Glu
        1075                1080                1085

Ala Gly Ala Ala Ala Gly Gly Glu Gly Glu Pro Glu Pro Ala Gly Thr
        1090                1095                1100

Arg Gly Asn Leu Ala His Arg His Pro Asn Asn Val His His Gly Arg
1105                1110                1115                1120

Arg Ala His Lys Ser Arg Ala Lys Gly His Arg Ala Gly Glu Ala Cys
            1125                1130                1135

Gly Lys Asn Arg Leu Lys Ala Leu Arg Gly Gly Ala Ala Gly Ala Leu
        1140                1145                1150

Glu Leu Leu Ser Ser Glu Ser Gly Ser Leu His Asn Ser Pro Thr Asp
        1155                1160                1165

Ser Tyr Leu Gly Ser Ser Arg Asn Ser Pro Gly Ala Gly Leu Gln Leu
        1170                1175                1180

Glu Gly Glu Pro Met Leu Thr Pro Ser Glu Gly Ser Asp Thr Ser Ala
1185                1190                1195                1200

Ala Pro Leu Ser Glu Ala Gly Arg Ala Gly Gln Arg Arg Ser Ala Ser
            1205                1210                1215

Arg Asp Ser Leu Lys Gly Gly Gly Ala Leu Glu Lys Glu Ser His Arg
            1220                1225                1230

Arg Ser Tyr Pro Leu Asn Ala Ala Ser Leu Asn Gly Ala Pro Lys Gly
            1235                1240                1245

Gly Lys Tyr Asp Asp Val Thr Leu Met Gly Ala Glu Val Ala Ser Gly
            1250                1255                1260

Gly Cys Met Lys Thr Gly Leu Trp Lys Ser Glu Thr Thr Val
1265                1270                1275

<210> SEQ ID NO 5
<211> LENGTH: 4068
<212> TYPE: DNA
<213> ORGANISM: homo sapiens

<400> SEQUENCE: 5
tctccccacc actctcttcg ggatattggg tgaagggctt gagcaaggat ggaactgtga      60
agggcatcat gaggggggcac tgagggtcag ccctgtggtt ccagagtgga acgggcat     120 cacagggtca cccccacctg ctcagcccac ctccccacctg cacacagagc cccacgtcag   180
agccaggctt ggaggagact cagggcagga aggtctgacg tggggctggg tggaccgttg    240
gccagcttct ccctgtaatc tccggaagta gagggtgggg gctgctgcct cgcacaactc    300 caggggcgc cattgacaaa gatgcaagct ggccccacca gtggtgaaag cggatgccca    360
gcacataaca gcaccttgtc ctgtctgtgt cctctctgtc tcttcaggct cttgagcaat   420
aacaagatca cggggctccg caatggctcc ttcctgggac tgtcactgct ggagaagctg    480
gacctgagga caacatcat cagcacagtg cagccgggcg ccttcctggg cctgggggag    540
ctgaagcgtt tagatctctc caacaaccgg attggctgtc tcacctccga gaccttccag   600
ggcctcccca ggcttctccg actaaacata tctggaaaca tcttctccag tctgcaacct   660
ggggtctttg atgagctgcc agcccttaag gttgtggact gggcaccgga gttcctgacc   720
tgtgactgcc acctgcgctg gctgctgccc tgggcccaga tcgctccct gcagctgtcg   780 gaacacacgc tctgtgctta ccccagtgcc ctgcatgctc aggccctggg cagcctccag    840
```

-continued

```
gaggcccagc tctgctgcga gggggccctg gagctgcaca cacaccacct catcccgtcc      900
ctacgccaag tggtgttcca gggggatcgg ctgcccttcc agtgctctgc cagctacctg      960
ggcaacgaca cccgcatccg ctggtaccac aaccgagccc ctgtggaggg tgatgagcag     1020
gcgggcatcc tcctggccga gagcctcatc cacgactgca ccttcatcac cagtgagctg     1080
acgctgtctc acatcggcgt gtgggcctca ggcgagtggg agtgcaccgt gtccatggcc     1140
caaggcaacg ccagcaagaa ggtggagatc gtggtgctgg agacctctgc ctcctactgc     1200
cccgccgagc gtgttgccaa caaccgcggg gacttcaggt ggccccgaac tctggctggc     1260
atcacagcct accagtcctg cctgcagtat cccttcacct cagtgcccct gggcgggggt     1320
gccccgggca cccgagcctc ccgccggtgt gaccgtgccg ccgctgggga ccaggggac      1380 tactcccact gtctctacac caacgacatc accaggtgc tgtacaccttt cgtgctgatg     1440 cccatcaatg cctccaatgc gctgaccctg gctcaccagc tgcgcgtgta cacagccgag     1500
gccgctagct tttcagacat gatggatgta gtctatgtgg ctcagatgat ccagaaattt     1560
ttgggttatg tcgaccagat caaagagctg gtagaggtga tggtggacat ggccagcaac     1620
ctgatgctgg tggacgagca cctgctgtgg ctggcccagc gcgaggacaa ggcctgcagc     1680
cgcatcgtgg gtgccctgga gcgcattggg ggggccgccc tcagccccca tgcccagcac     1740
atctcagtga atgcgaggaa cgtggcattg gaggcctacc tcatcaagcc gcacagctac     1800
gtgggcctga cctgcacagc cttccagagg agggagggag gggtgccggg cacacggcca     1860
ggaagccctg ccagaacccc ccacctgagc ccgagcccc cagctgacca gcagctccgc     1920
ttccgctgca ccaccgggag gcccaatgtt tctctgtcgt ccttccacat caagaacagc     1980
gtggccctgg cctccatcca gctgccccg agtctattct catcccttcc ggctgccctg     2040 gctccccgg tgcccccaga ctgcaccctg caactgctcg tcttccgaaa tggccgcctc     2100
ttccacagcc acagcaacac ctcccgccct ggagctgctg ggcctggcaa gaggcgtggc     2160
gtggccaccc ccgtcatctt cgcaggaacc agtggctgtg gcgtgggaaa cctgacagag     2220
ccagtggccg tttcgctgcg gcactgggct gagggagccg aacctgtggc cgcttggtgg     2280
agccaggagg ggcccgggga ggctgggggc tggacctcgg agggctgcca gctccgctcc     2340
agccagccca atgtcagcgc cctgcactgc cagcacttgg gcaatgtggc cgtgctcatg     2400
gagctgagcg cctttcccag ggaggtgggg ggcgccgggg cagggctgca ccccgtggta     2460
tacccctgca cggccttgct gctgctctgc ctcttcgcca ccatcatcac ctacatcctc     2520
aaccacagct ccatccgtgt gtcccggaaa ggctggcaca tgctgctgaa cttgtgcttc     2580
cacatagcca tgacctctgc tgtctttgcg ggggcatca cactcaccaa ctaccagatg     2640
gtctgccagg cggtgggcat caccctgcac tactcctccc tatccacgct gctctggatg     2700
ggcgtgaagc gcgagtgct ccataaggag ctcacctgga gggcaccccc tccgcaagaa     2760
ggggacccca ctctgcctac tcccagtcct atgctccgct gctggctggt gtggcgtcca     2820
agccttggcg cctt ctacat ccctgtggct ttgattctgc tcatcacctg gatctatttc     2880
ctgtgcgccg ggctacgctt acgggtcct ctggcacaga accccaaggc gggcaacagc     2940
agggcctccc tggaggcagg ggaggagctg aggggttcca ccaggctcag ggcagcggc     3000 cccctcctga gtgactcagg ttcccttctt gctactggga gcgcgcgagt ggggacgccc     3060
gggcccccgg aggatggtga cagcctctat tctccgggag tccagctagg ggcgctggtg     3120
accacgcact tcctgtactt ggccatgtgg ggcctgcggg gctctggcagt gtcccagcgc     3180 tggctgcccc gggtggtgtg cagctgcttg tacgggtggg cagcctccgc cctgggcctc     3240
```

-continued

```
ttcgtcttca ctcaccactg tgccaggcgg agggacgtga gagcctcgtg gcgcgcctgc    3300
tgcccccctg cctctcccgc ggcccccat gccccgcccc gggccctgcc cgccgccgca     3360
gaggacggtt ccccggtgtt cggggagggg ccccctccc tcaagtcctc cccaagcggc     3420
agcagcggcc atccgctggc tctgggcccc tgcaagctca ccaacctgca gctggcccag    3480
agtcaggtgt gcgaggcggg ggcggcggcc ggcggggaag gagagccgga gccggcgggc    3540
acccggggaa acctcgccca ccgccacccc aacaacgtgc accacgggcg tcgggcgcac    3600
aagagccggg ccaagggaca ccgcgcgggg gaggcctgcg gcaagaaccg gctcaaggcc    3660
ctgcgcgggg gcgcggcggg ggcgctggag ctgctgtcca gcgagagcgg tagtctgcac    3720
aacagcccca ccgacagcta cctgggcagc agccgcaaca gcccgggcgc cggcctgcag    3780
ctggaaggcg agcccatgct cacgccgtcc gagggcagcg acaccagcgc cgcgccgctt    3840
tctgaggcgg gccgggcagg ccagcgccgc agcgccagcc gcgacagtct caagggcggc    3900
ggcgcgctgg agaaggagag ccatcgccgc tcgtacccgc tcaacgccgc cagcctaaac    3960
ggcgccccca aggggggcaa gtacgacgac gtcaccctga tgggcgcgga ggtagccagc    4020
ggcggctgca tgaagaccgg actctggaag agcgaaacta ccgtctaa                 4068
```